United States Patent
Chen et al.

(10) Patent No.: US 11,191,488 B2
(45) Date of Patent: Dec. 7, 2021

(54) APPARATUS FOR IMPROVING USABILITY AND ACCURACY FOR PHYSIOLOGICAL MEASUREMENT

(71) Applicant: iXensor CO., LTD., Taipei (TW)

(72) Inventors: Yenyu Chen, Taipei (TW); Yao Ching Tsai, Taipei (TW); Jheng Long Jiang, Taipei (TW); Chieh Yu Lin, Taipei (TW); Chun Hun Shen, Taipei (TW)

(73) Assignee: IXENSOR CO., LTD.

( * ) Notice: Subject to any disclaimer, the term of this patent is extended or adjusted under 35 U.S.C. 154(b) by 84 days.

(21) Appl. No.: 16/494,315

(22) PCT Filed: Mar. 16, 2018

(86) PCT No.: PCT/CN2018/079304
§ 371 (c)(1),
(2) Date: Sep. 16, 2019

(87) PCT Pub. No.: WO2018/166530
PCT Pub. Date: Sep. 20, 2018

(65) Prior Publication Data
US 2020/0375543 A1    Dec. 3, 2020

Related U.S. Application Data

(60) Provisional application No. 62/472,585, filed on Mar. 17, 2017.

(51) Int. Cl.
*A61B 5/1455*    (2006.01)
*A61B 5/00*    (2006.01)
(Continued)

(52) U.S. Cl.
CPC .......... *A61B 5/6898* (2013.01); *A61B 5/0059* (2013.01); *A61B 5/14532* (2013.01);
(Continued)

(58) Field of Classification Search
None
See application file for complete search history.

(56) References Cited

U.S. PATENT DOCUMENTS

2005/0201898 A1    9/2005 Borich et al.
2005/0277164 A1    12/2005 Drucker et al.
(Continued)

FOREIGN PATENT DOCUMENTS

CN    103315747 A    9/2013
CN    103983572 A    8/2014
(Continued)

OTHER PUBLICATIONS

The Extended European Search Report, International application No. PCT/CN2018/079304, dated Dec. 31, 2020.
(Continued)

*Primary Examiner* — Paul S Hyun
(74) *Attorney, Agent, or Firm* — Su IP Consulting

(57) ABSTRACT

Example apparatus are provided to measure characteristics of a test strip. The apparatus may include an accessory for a mobile device to measure characteristics of a test strip. The accessory may include a mobile device adaptor and a test strip adaptor. The mobile device adaptor may include a first sheath and a second sheath coupled to the first sheath to secure the mobile device. The test strip adaptor may be detachably coupled to the mobile device adapter. The test strip adaptor is configured to receive different types of test strips.

9 Claims, 33 Drawing Sheets

(51) Int. Cl.
*A61B 5/145* (2006.01)
*A61B 5/15* (2006.01)
*G01N 21/84* (2006.01)
*G03B 17/56* (2021.01)
*B01L 9/00* (2006.01)
*G01N 33/487* (2006.01)

(52) U.S. Cl.
CPC .......... *A61B 5/150358* (2013.01); *B01L 9/00* (2013.01); *G01N 21/8483* (2013.01); *G01N 33/48778* (2013.01); *G03B 17/565* (2013.01); *A61B 2560/0233* (2013.01); *B01L 2300/041* (2013.01); *B01L 2300/0825* (2013.01)

(56) References Cited

U.S. PATENT DOCUMENTS

| | | |
|---|---|---|
| 2006/0222567 A1 | 10/2006 | Kloephfer et al. |
| 2013/0273528 A1 | 10/2013 | Ehrenkranz |
| 2014/0072189 A1* | 3/2014 | Jena ............... A61B 5/1455 |
| | | 382/128 |
| 2014/0170761 A1 | 6/2014 | Crawford et al. |
| 2014/0286550 A1 | 9/2014 | Beule et al. |
| 2014/0296112 A1 | 10/2014 | O'Driscoll et al. |
| 2016/0080548 A1* | 3/2016 | Erickson ........... H04M 1/72409 |
| | | 455/556.1 |
| 2016/0131592 A1 | 5/2016 | Cooper |
| 2016/0381265 A1* | 12/2016 | Cong ................... H04N 5/332 |
| | | 348/371 |

FOREIGN PATENT DOCUMENTS

| | | |
|---|---|---|
| JP | 2017506324 A | 3/2017 |
| TW | 201840292 A | 11/2018 |
| WO | 2012037567 A1 | 3/2012 |
| WO | 2017041129 A1 | 3/2017 |
| WO | 2018166530 | 9/2018 |

OTHER PUBLICATIONS

International Search Report and Written Opinion of the International Searching Authority, International application No. PCT/CN2018/079304, dated May 30, 2018.

* cited by examiner

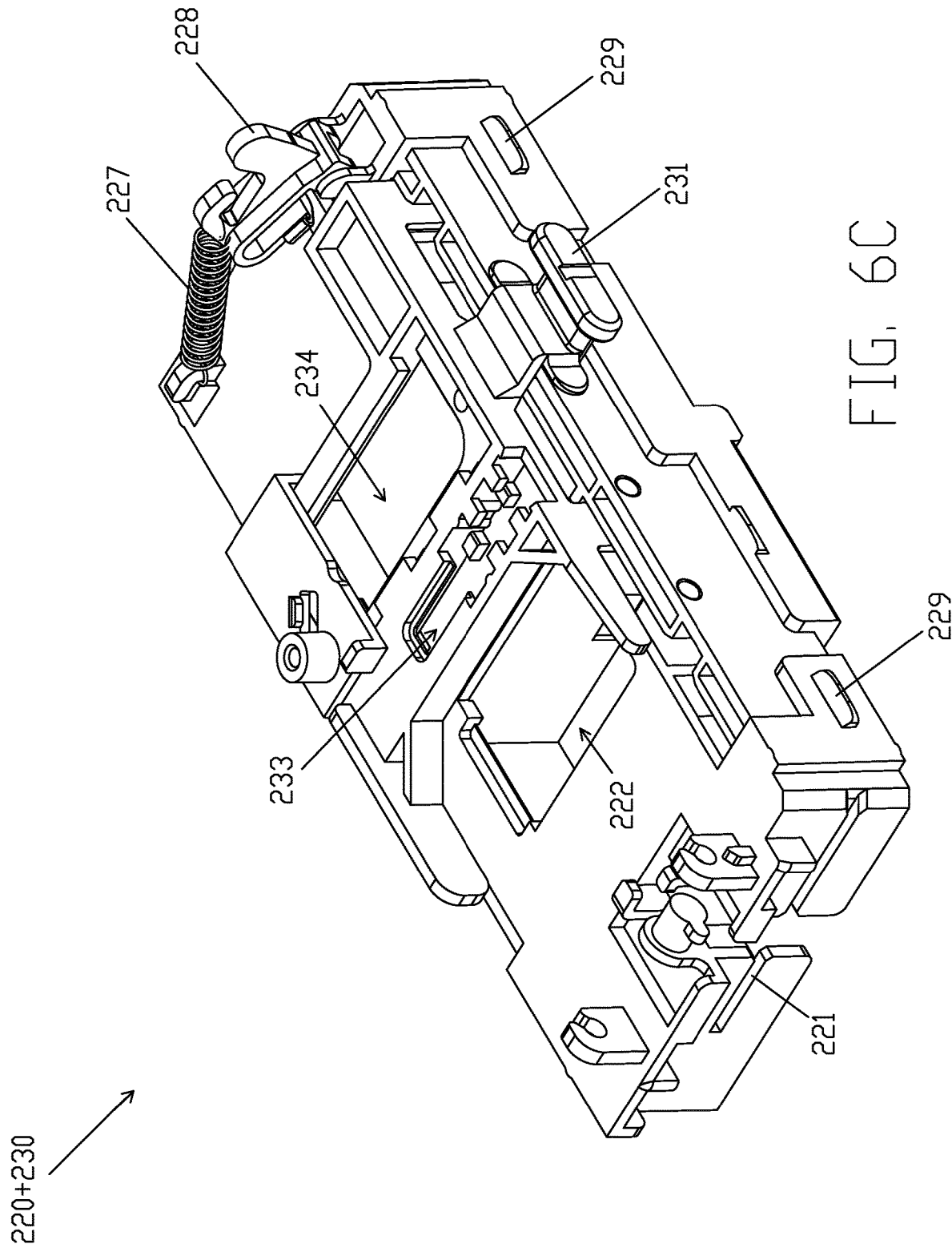

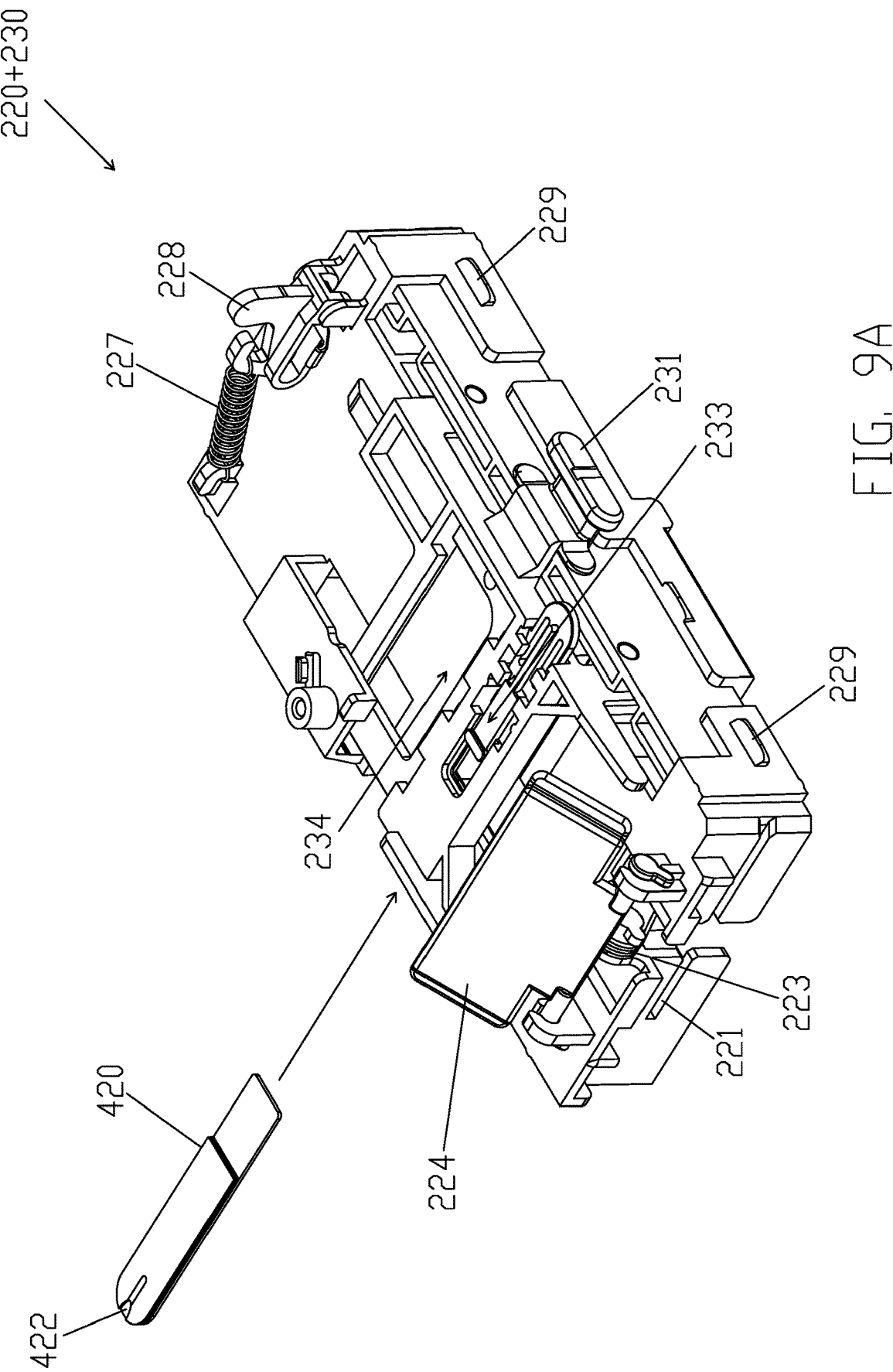

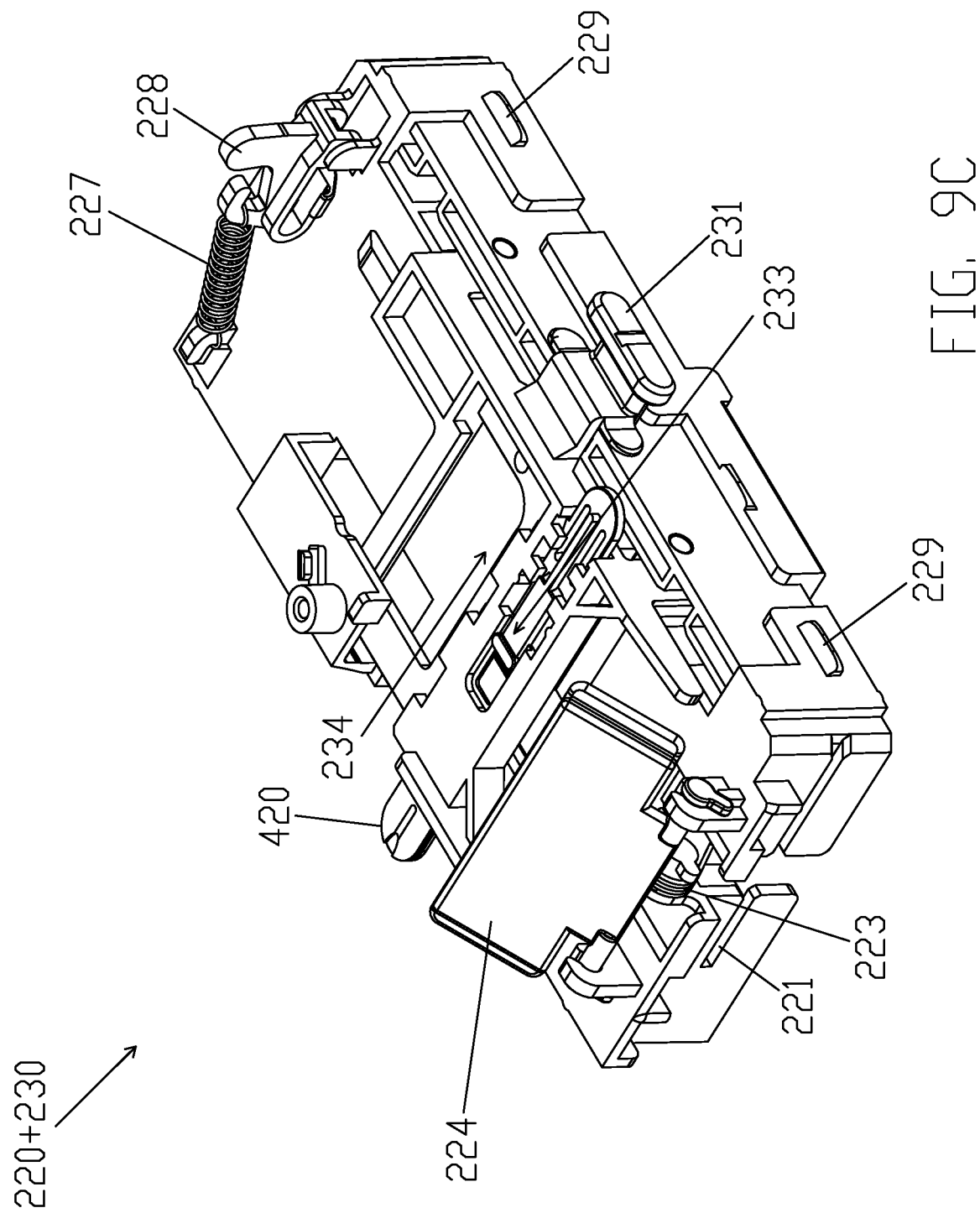

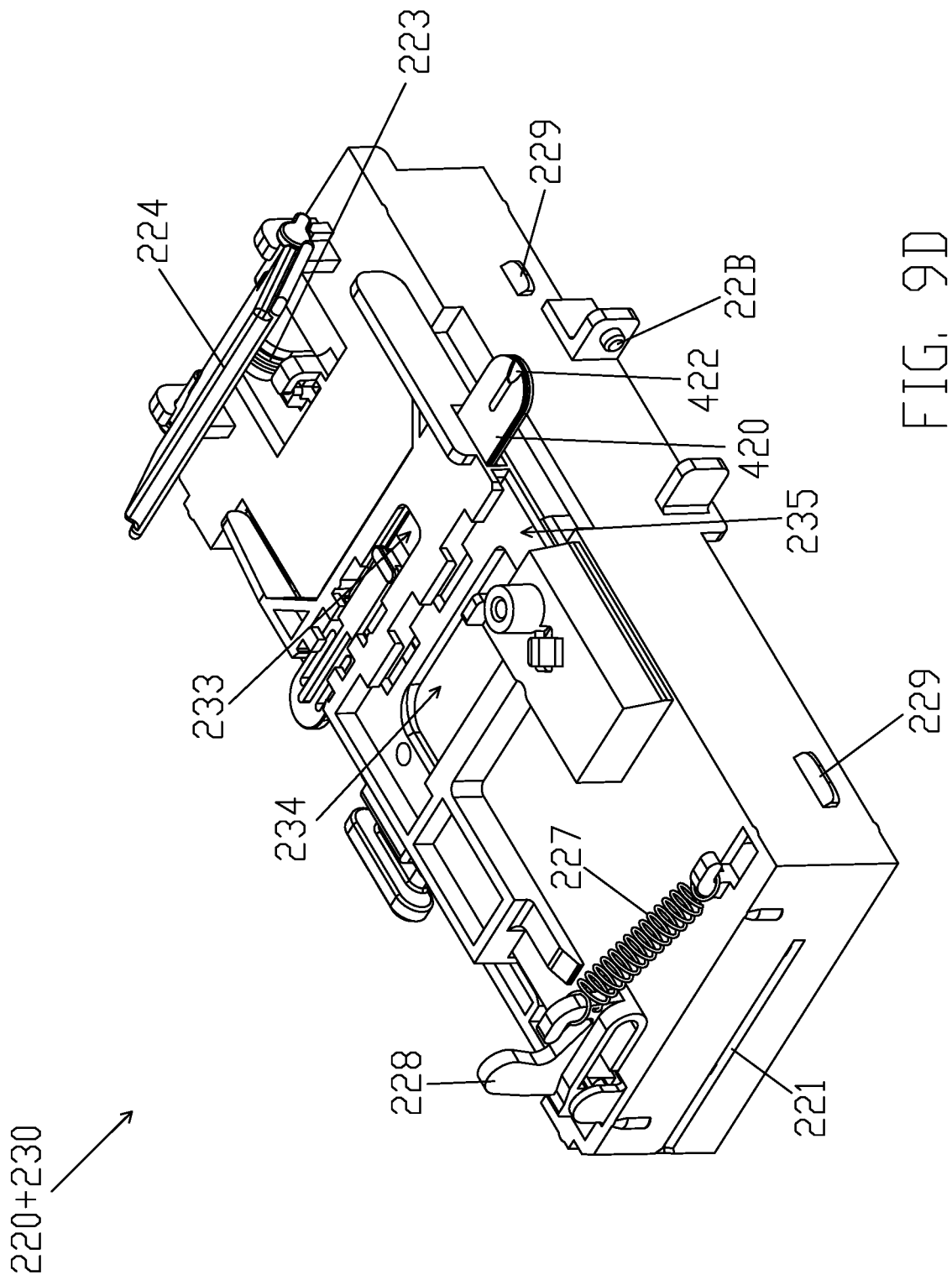

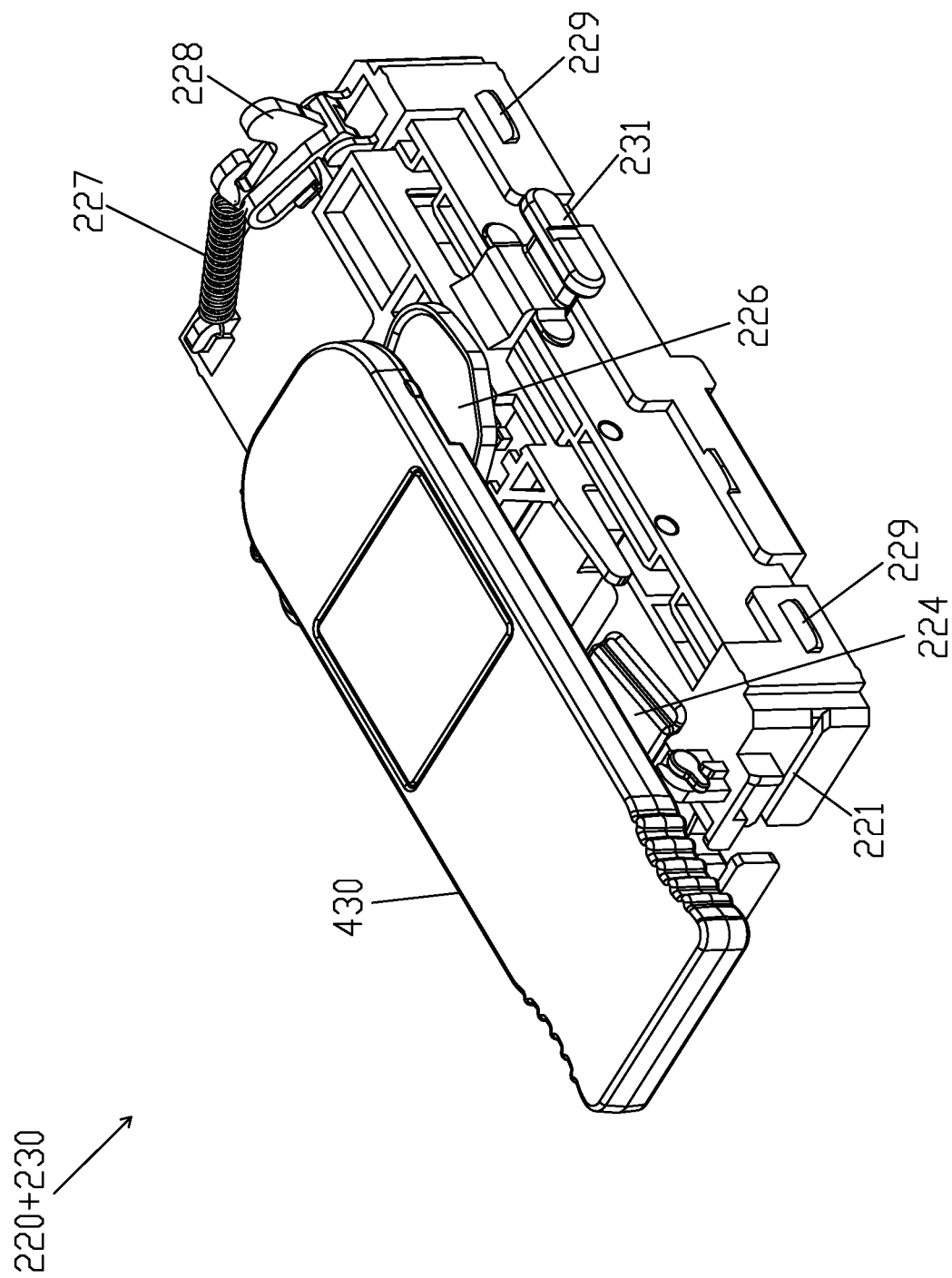

APPARATUS FOR IMPROVING USABILITY AND ACCURACY FOR PHYSIOLOGICAL MEASUREMENT

CROSS-REFERENCE TO RELATED APPLICATION

The present application is a U.S. national stage filing under 35 U.S. C. § 371 of International Application No. PCT/CN2018/079304, filed Mar. 16, 2018, which claims the benefit of U.S. Provisional Application No. 62/472,585 filed Mar. 17, 2017. The International Application and the U.S. Provisional Application above are incorporated by reference in their entirety.

BACKGROUND

In recent years, in-vitro diagnosis (IVD) devices, especially blood glucose meters, have gained wide adoption among patients with chronic diseases. In order to take measurements, patients usually have to carry standalone IVD devices with them at all times.

For typical IVD measurements, test strips consisting enzyme and reagent are used. Upon receiving the sample fluid, the test strip's characteristics, such as electrical impedance or color, change according to the concentration of the targeted analyte, such as blood glucose or blood cholesterol.

Optochemistry-based IVD systems usually comprises test strips that change color according to the concentration of analyte received, specific light sources that illuminate on strips, optical sensors that detect scattering light, and light-isolating cases.

These existing IVD devices tend to work with a particular type of test strip. For patients needing to conduct multiple tests involving different types of test strips, they would be required to obtain and carry multiple IVD devices with them.

SUMMARY

In examples of the present disclosure, apparatus are provided to measure characteristics of a test strip. The apparatus may include an accessory for a mobile device to measure characteristics of a test strip. The accessory may include a mobile device adaptor and a test strip adaptor. The mobile device adaptor may include a first sheath and a second sheath coupled to the first sheath to secure the mobile device. The test strip adaptor may be detachably coupled to the mobile device adapter. The test strip adaptor is configured to receive different types of test strips.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are therefore not to be considered limiting of its scope. The disclosure will be described with additional specificity and detail through use of the accompanying drawings.

FIGS. 6A, 6B and 6C illustrate perspective views of main bracket 220 and test strip bracket 230, according to some embodiments of the present disclosure.

FIG. 9A illustrates front perspective view of main bracket 220 and test strip bracket 230 prior to small sized test strip 420 being inserted into first detecting opening 233 and second inserting entry 215, according to some embodiments of the present disclosure.

FIG. 9C illustrates front perspective view of main bracket 220 and test strip bracket 230 after small sized test strip 420 being inserted into first detecting opening 233 and second inserting entry 215, according to some embodiments of the present disclosure.

FIG. 9D illustrates back perspective view of main bracket 220 and test strip bracket 230 after small sized test strip 420 being inserted into first detecting opening 233 and second inserting entry 215, according to some embodiments of the present disclosure.

FIG. 10C illustrates front perspective view of main bracket 220 and test strip bracket 230 after calibration test strip 430 being inserted into first inserting entry 214, according to some embodiments of the present disclosure.

DETAILED DESCRIPTION

Figure 1:
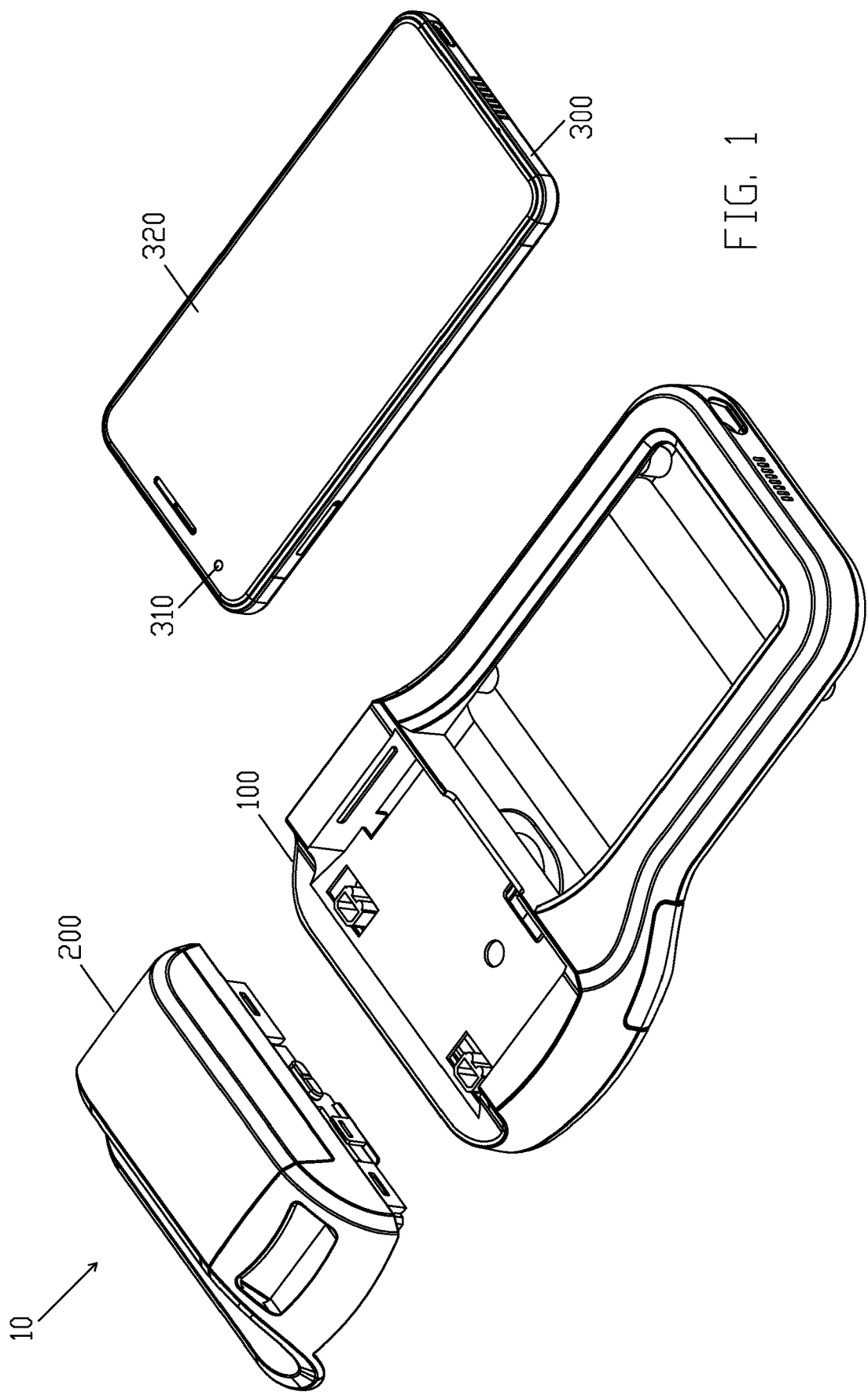
FIG. 1 illustrates a perspective view of mobile device accessory 10, according to some embodiments of the present disclosure.

In the following detailed description, reference is made to the accompanying drawings, which form a part hereof. In the drawings, similar symbols typically identify similar components and same numerals typically identify same components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated herein.

FIG. 1 illustrates a perspective view of mobile device accessory 10, according to some embodiments of the present disclosure. In some embodiments, mobile device accessory 10 includes mobile device adaptor 100, test strip adaptor 200 and mobile device 300. Mobile device adaptor 100 may be configured to lock with test strip adaptor 200. Mobile device adaptor 100 may be also configured to receive mobile device 300. In some embodiments, mobile device 300 includes camera 310 and screen 320.

Figure 2A:
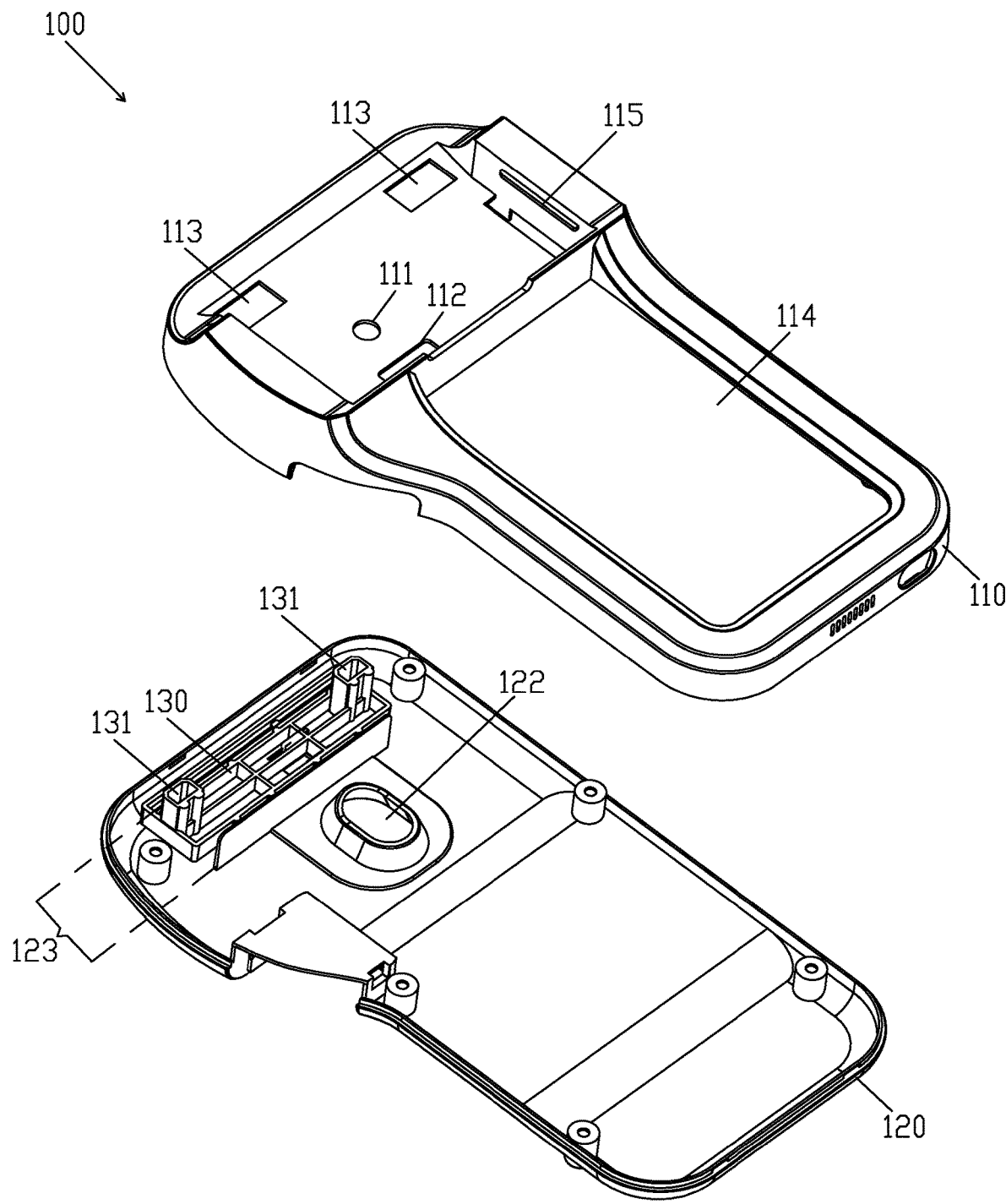
FIG. 2A illustrates an exploded top perspective view of mobile device adaptor 100, according to some embodiments of the present disclosure.
Figure 2B:
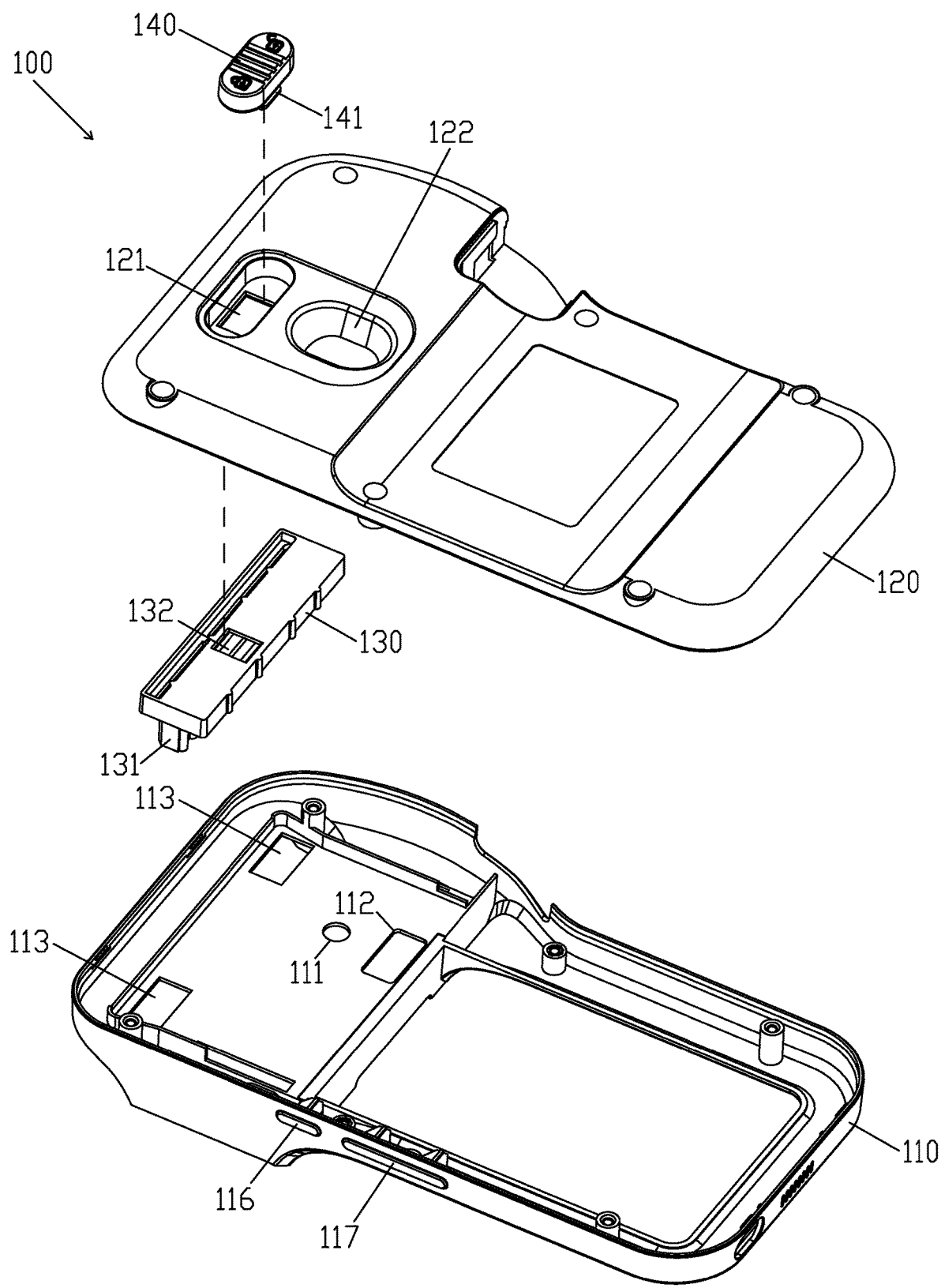
FIG. 2B illustrates an exploded bottom perspective view of mobile device adaptor 100, according to some embodiments of the present disclosure.

FIG. 2A illustrates an exploded top perspective view of mobile device adaptor 100, according to some embodiments of the present disclosure. FIG. 2B illustrates an exploded bottom perspective view of mobile device adaptor 100, according to some embodiments of the present disclosure. In conjunction with FIG. 2A and FIG. 2B, mobile device adaptor 100 may include first sheath (e.g., top sheath 110), second sheath (e.g., bottom sheath 120), a locking mechanism (e.g., latch 130 and knob 140). Top sheath 110 may be configured to couple to bottom sheath 120. Top sheath 110 and bottom sheath 120, once coupled to one another, secure mobile device 300.

Referring to FIG. 2A, in some embodiments, top sheath 110 defines camera hole 111, illuminating screen opening 112, a set of latch openings 113, a display opening 114 and a set of guiding elements 115. In some embodiments, bottom sheath 120 includes latch guiding groove 123.

In some embodiments, in conjunction with FIG. 1, in response to mobile device 300 being received between top sheath 110 and bottom sheath 120, camera hole 111 and illuminating screen opening 112 are configured to respectively correspond to camera 310 and a first portion of screen 320 of mobile device 300. First portion of screen 320 is configured to illuminate a reaction area of a test strip and camera 310 is configured to capture an image of the reaction area. In addition, display opening 114 may correspond to a second portion of screen 320 to provide a display for a user.

Referring to FIG. 2B, in some embodiments, top sheath 110 includes power button 116 and volume button 117 configured for a user to control mobile device 300 received between top sheath 110 and bottom sheath 120. In some embodiments, bottom sheath 120 defines first sheath opening 121 and second sheath opening 122. First sheath opening 121 may be configured to receive knob 140. Second sheath opening 122 may be configured to correspond to another camera (not shown) of mobile device 300.

In FIG. 2B, in some embodiments, latch 130 is configured to dispose between top sheath 110 and bottom sheath 120. Latch 130 may include a set of latch protruding elements 131. Latch protruding elements 131 may be configured to insert through latch openings 113. In some embodiments, knob 140 may include knob clip 141, which can be coupled to a corresponding knob opening 132 on latch 130. In conjunction with FIG. 2A, latch 130 may be received in latch guiding groove 123 and configured to slide along latch guiding groove 123 by sliding knob 140 in first sheath opening 121.

Figure 3A:
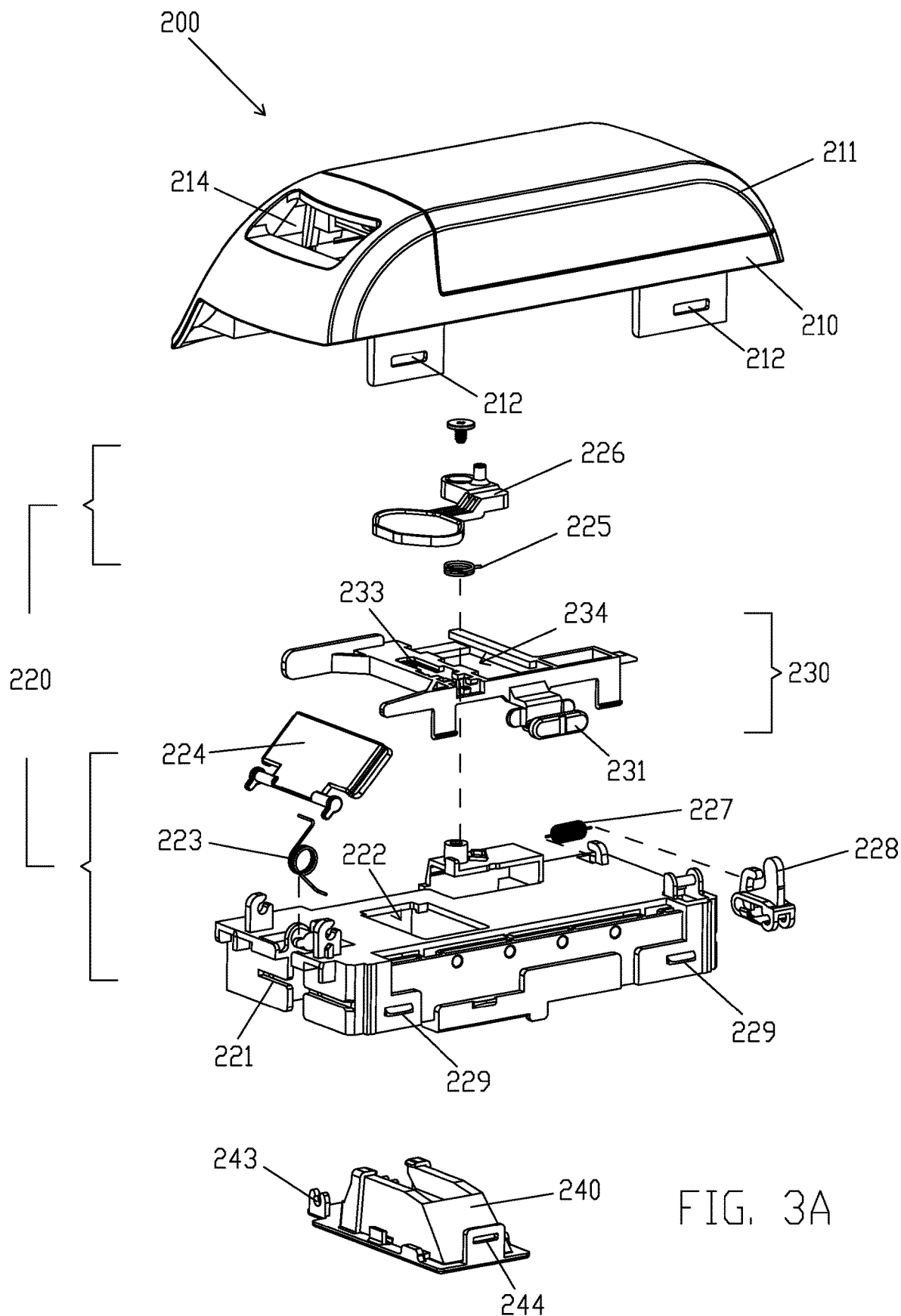
FIG. 3A illustrates an exploded front perspective view of test strip adaptor 200, according to some embodiments of the present disclosure.
Figure 3B:
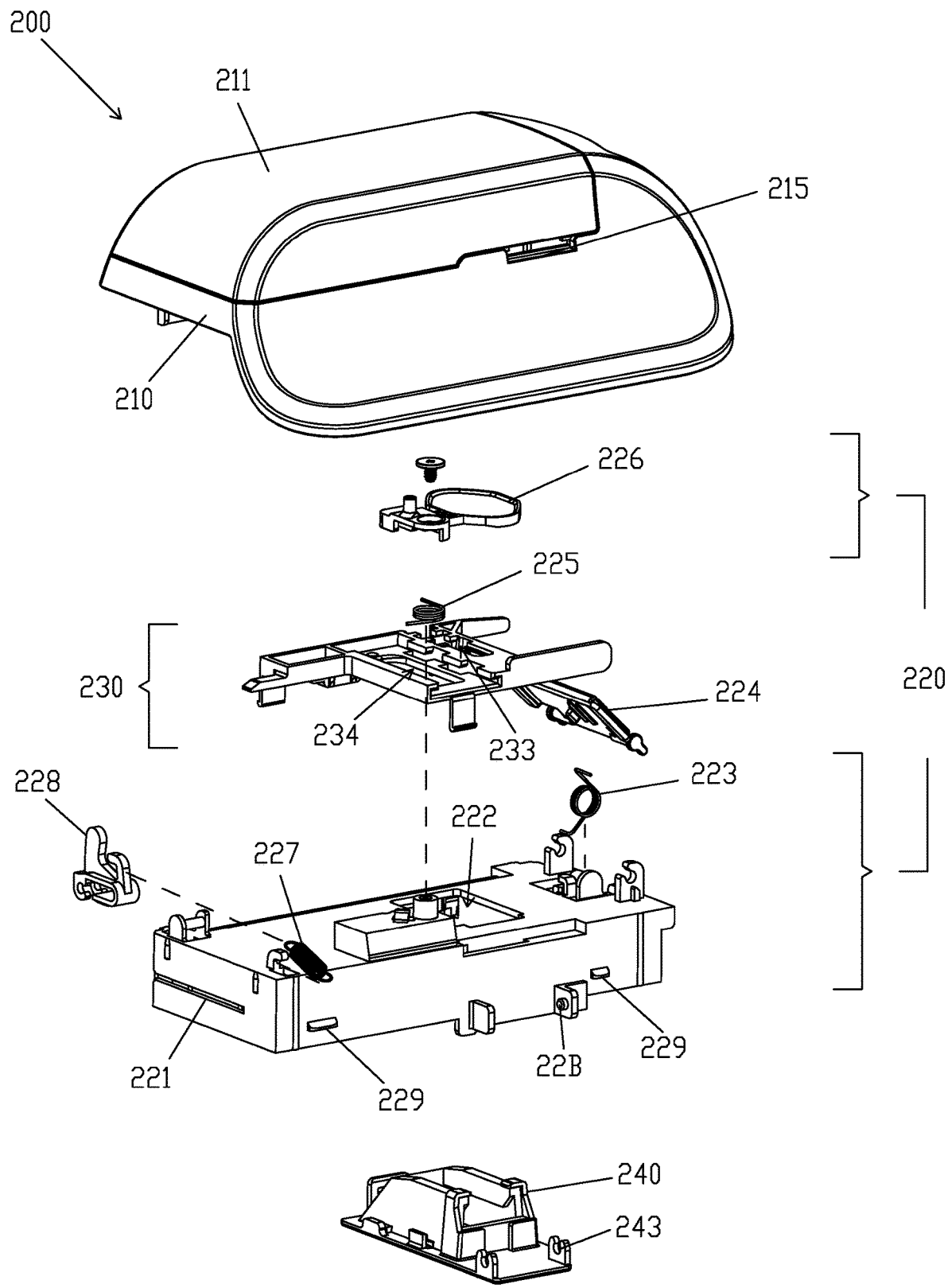
FIG. 3B illustrates an exploded back perspective view of test strip adaptor 200, according to some embodiments of the present disclosure.

FIG. 3A illustrates an exploded front perspective view of test strip adaptor 200, according to some embodiments of the present disclosure. FIG. 3B illustrates an exploded back perspective view of test strip adaptor 200, according to some embodiments of the present disclosure. In some embodiments, test strip adaptor 200 includes case 210, main bracket 220, test strip bracket 230 and light guide 240. In some embodiments, case 210 is configured to engage with main bracket 220. In some other embodiments, in response to case 210 being engaged with main bracket 220, test strip bracket 230 is configured to dispose in a space defined by engaged case 210 and main bracket 220. In addition, light guide 240 is configured to couple to one side of main bracket 220, while test strip bracket 230 is coupled to another side of main bracket 220.

In conjunction with FIGS. 3A and 3B, in some embodiments, case 210 is coupled to sliding module 211 via a sliding mechanism. In addition, case 210 defines a set of connecting openings 212, first inserting entry 214 and second inserting entry 215. Sliding module 211 may be configured to cover or reveal second inserting entry 215 as sliding module 211 slides from one side of case 210 to another side of case 210.

In conjunction with FIGS. 3A and 3B, in some embodiments, main bracket 220 defines a set of main bracket guiding grooves 221 and main detecting opening 222. In addition, in some embodiments, main bracket 220 includes first torsion spring 223, first door 224, second torsion spring 225, second door 226, tension spring 227, lock 228, a set of first connecting elements 229, and pivot 22B.

In conjunction with FIGS. 3A and 3B, in some embodiments, test strip bracket 230 may include handle 231. In addition, in some embodiments, test strip bracket 230 defines first detecting opening 233 and second detecting opening 234. In conjunction with FIGS. 3A and 3B, in some embodiments, light guide 240 includes a set of notches 243 and defines light guide connecting opening 244.

In some embodiments, case 210 is configured to engage with main bracket 220. Referring back to FIG. 3A, connecting openings 212 are extended at one side of case 210. In some embodiments, connecting openings 212 correspond to and are configured to engage with first connecting elements 229 of main bracket 220. In response to engagement of first connecting elements 229 and connecting openings 212, case 210 is engaged with main bracket 220.

In some embodiments, some elements of main bracket 220 are described here in detail. Main detecting opening 222 may be a through opening defined on main bracket 220. In addition, in conjunction with FIG. 2A, main detecting opening 222 is configured to correspond to and align with camera hole 111 and illuminating screen opening 112 of top sheath 110.

In some embodiments, referring to FIG. 3A, at one side of main bracket 220, one end of first torsion spring 223 is configured to engage with main bracket 220. The other end of first torsion spring 223 is configured to engage with first door 224. In some embodiments, first door 224 is configured to cover first inserting entry 214 when there is no test strip inserted into first inserting entry 214. In some embodiments, when a test strip is inserted into first inserting entry 214, the test strip pushes first door 224 away so that the test strip can reach main detecting opening 222.

In some embodiments, referring to FIG. 3A, second torsion spring 225 is disposed on main bracket 220. One end of second torsion spring 225 may be engaged with second door 226 so that second door 226 is configured to be in a first position to cover main detecting opening 222 when second torsion spring 225 maintains a first torsion force or in a second position to reveal main detecting opening 222 when second torsion spring 225 maintains a second torsion force. In some embodiments, when second door 226 is in the first position, second door 226 may cover main detecting opening 222 and protect camera 310 from being polluted by potential pollutants (e.g., dust or blood on test strip). In some embodiments, when second door 226 is in the second position, second door 226 may leave main detecting opening 222 at least partially unobstructed so that camera 310 may have a light path through main detecting opening 222 to capture one or more images of the reaction area of the test strip. In some embodiments, in response to a test strip being inserted into second inserting entry 215, the test strip may push second door 226 from the first position to the second position to reveal main detecting opening 222.

In some embodiments, referring to FIGS. 3A and 3B, at the other side of main bracket 220 opposite from the side at which first torsion spring 223 is engaged, tension spring 227 is configured to engage with lock 228 of main bracket 220. The engagement of tension spring 227 and lock 228 is configured to lock or unlock of sliding module 211 with case 210.

In some embodiments, referring to FIG. 3A, test strip bracket 230 includes handle 231. Handle 231 is at one side of test strip bracket 230. In addition, handle 231 is manually shifted on main bracket 220. Test strip bracket 230 may define first detecting opening 233 and second detecting opening 234. The detecting openings 233 and 234 will be further described in detail below.

Figure 3C:
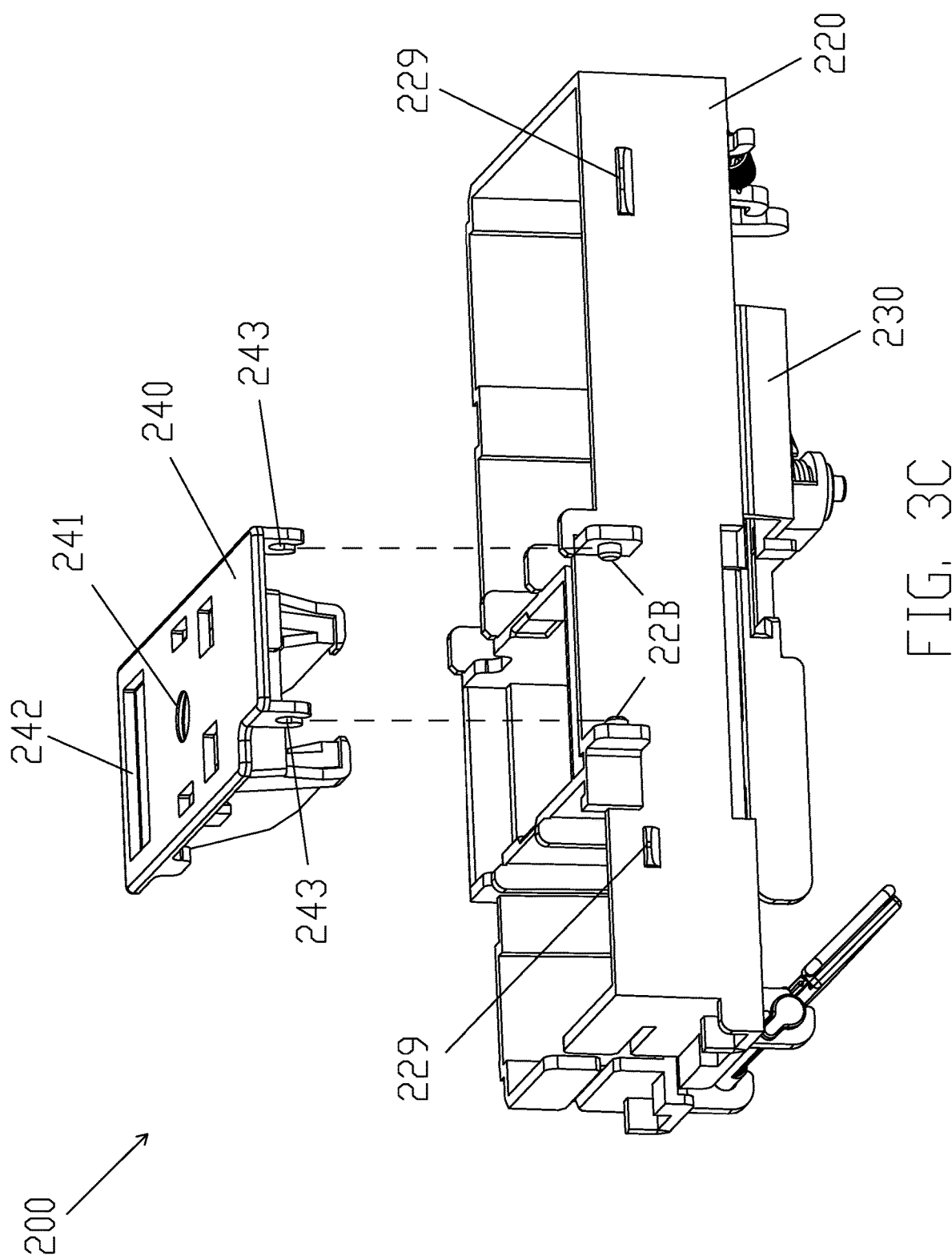
FIG. 3C illustrates an exploded bottom-front perspective view of test strip adaptor 200, according to some embodiments of the present disclosure.
Figure 3D:
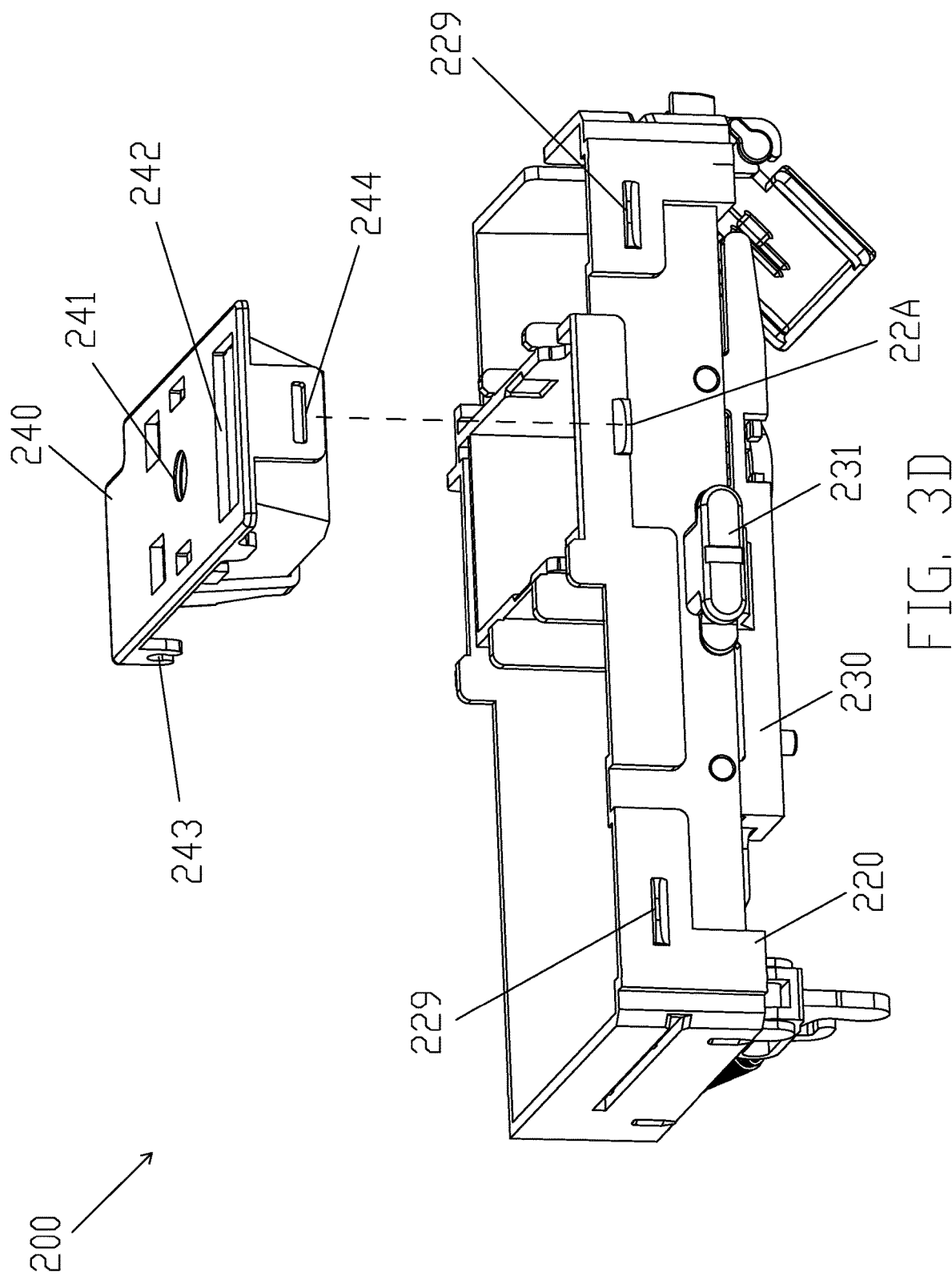
FIG. 3D illustrates an exploded bottom-back perspective view of test strip adaptor 200, according to some embodiments of the present disclosure.

As set forth above, test strip bracket 230 may be configured to dispose in a space defined by engaged case 210 and main bracket 220. FIG. 3C illustrates an exploded bottom-front perspective views of test strip adaptor 200 (case 210 not included for clarity) when the test strip bracket 230 is disposed in main bracket 220, according to some embodiments of the present disclosure. FIG. 3D illustrates an exploded bottom-back perspective views of test strip adaptor 200 (case 210 not included for clarity) when the test strip bracket 230 is disposed in main bracket 220, according to some embodiments of the present disclosure. In FIG. 3D, light guide 240 includes notches 243 and defines light guide connecting opening 244. In conjunction with FIG. 3B, notches 243 may be engaged with pivots 22B to secure light guide 240 to main bracket 220. Similarly, referring back to FIG. 3D, light guide connecting opening 244 is also configured to engage with first connecting element 22A of main bracket 220 to secure light guide 240 to main bracket 220.

In some embodiments, in FIG. 3C, light guide 240 further defines light guide camera opening 241 and light guide illuminating screen opening 242. In some embodiments, in conjunction with FIG. 3A, light guide camera opening 241 and light guide illuminating screen opening 242 are both unobstructed from main detecting opening 222 of main bracket 220. In addition, in conjunction with FIG. 2A, light guide camera opening 241 may correspond to camera hole 111 of top sheath 110. Similarly, light guide illuminating screen opening 242 may correspond to illuminating screen opening 112 of top sheath 110.

Figure 4:
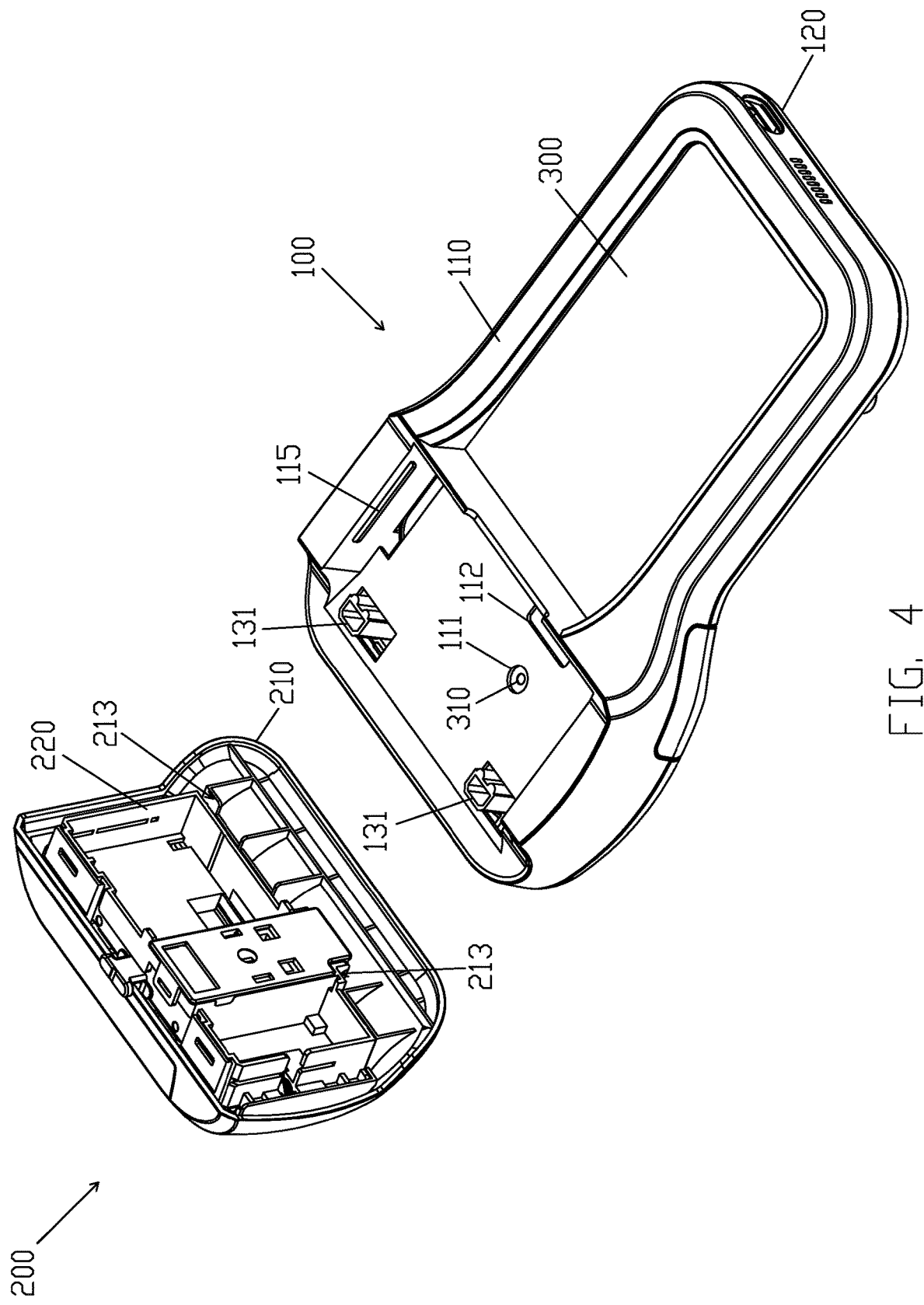
FIG. 4 illustrates a perspective view of mobile device adaptor 100 and test strip adaptor 200, according to some embodiments of the present disclosure.

FIG. 4 illustrates a perspective view of mobile device adaptor 100 and test strip adaptor 200, according to some embodiments of the present disclosure. As set forth above, test strip adaptor 200 may be locked with mobile device adaptor 100. In conjunction with FIGS. 2A and 2B, case 210 may further include latch housings 213 to receive latch protruding elements 131. In some embodiments, knob 140 is configured to actuate the movement of latch protruding elements 131 in latch housings 213 to lock test strip adaptor 200 to mobile device adaptor 100 to or to unlock test strip adaptor 200 from mobile device adaptor 100.

Figure 5A:
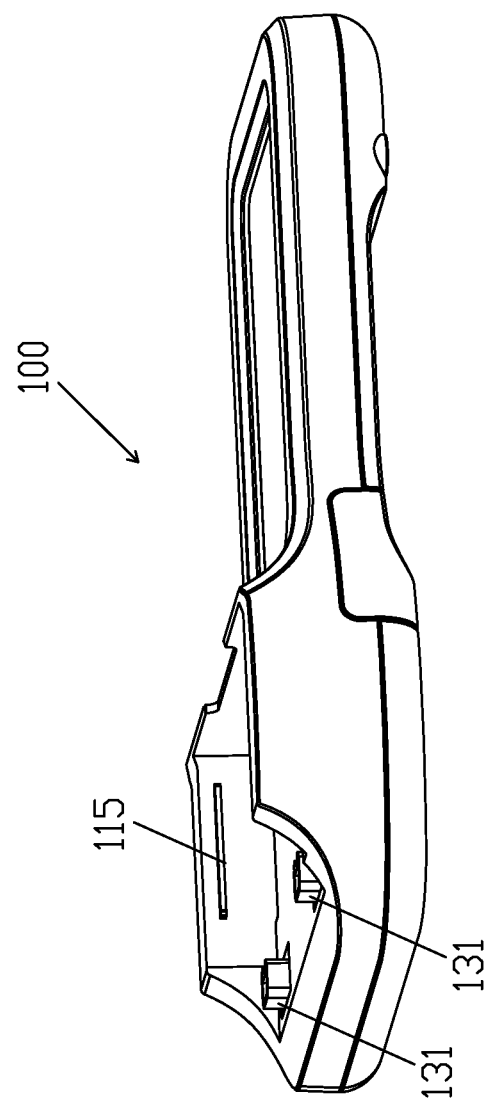
FIGS. 5A and 5B illustrate another two perspective views of mobile device adaptor 100 and test strip adaptor 200, according to some embodiments of the present disclosure.
Figure 5A:
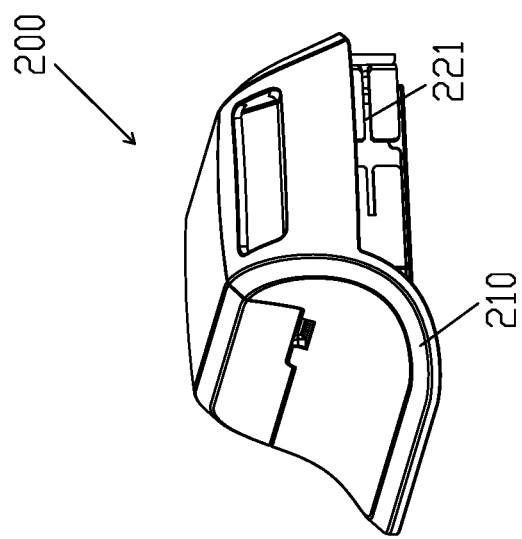
Figure 5B:
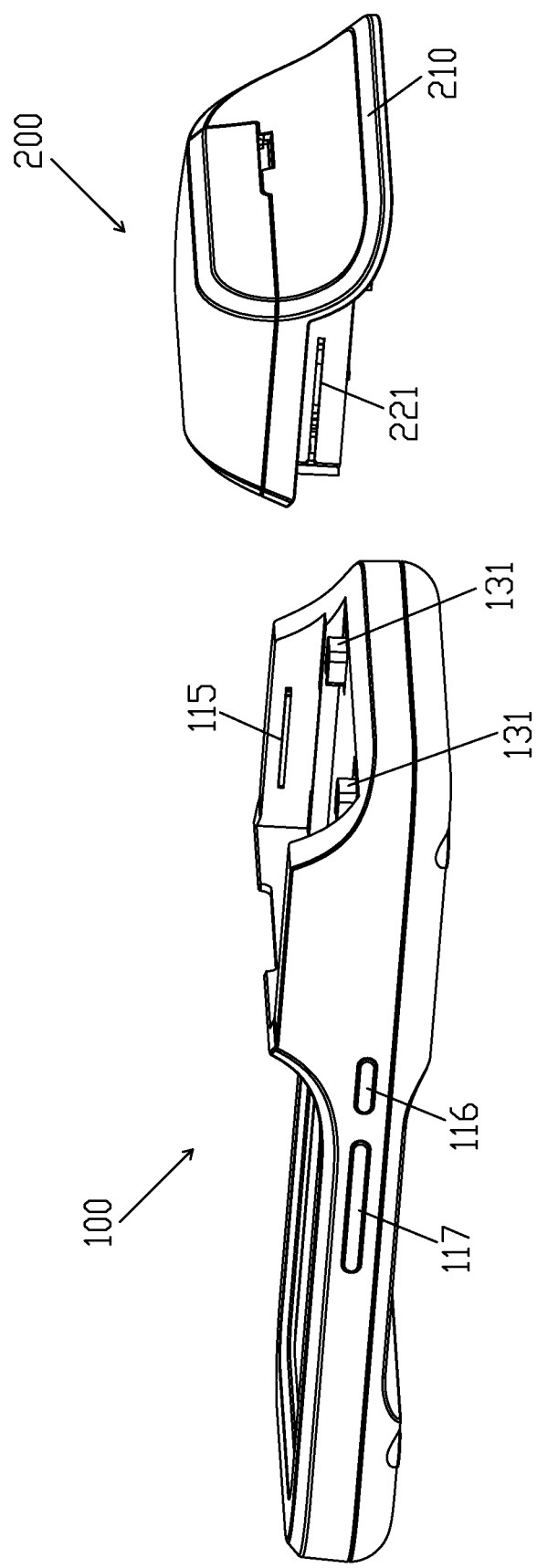

FIGS. 5A and 5B illustrate another two perspective views of mobile device adaptor 100 and test strip adaptor 200, according to some embodiments of the present disclosure. In conjunction with FIGS. 3A and 3B, main bracket guiding grooves 221 of main bracket 220 are configured to receive guiding elements 115 of top sheath 110. Therefore, in conjunction with FIG. 4, before locking test strip adaptor 200 to mobile device adaptor 100, test strip adaptor 200 may be guided, by guiding elements 115 toward mobile device adaptor 100.

Figure 6A:
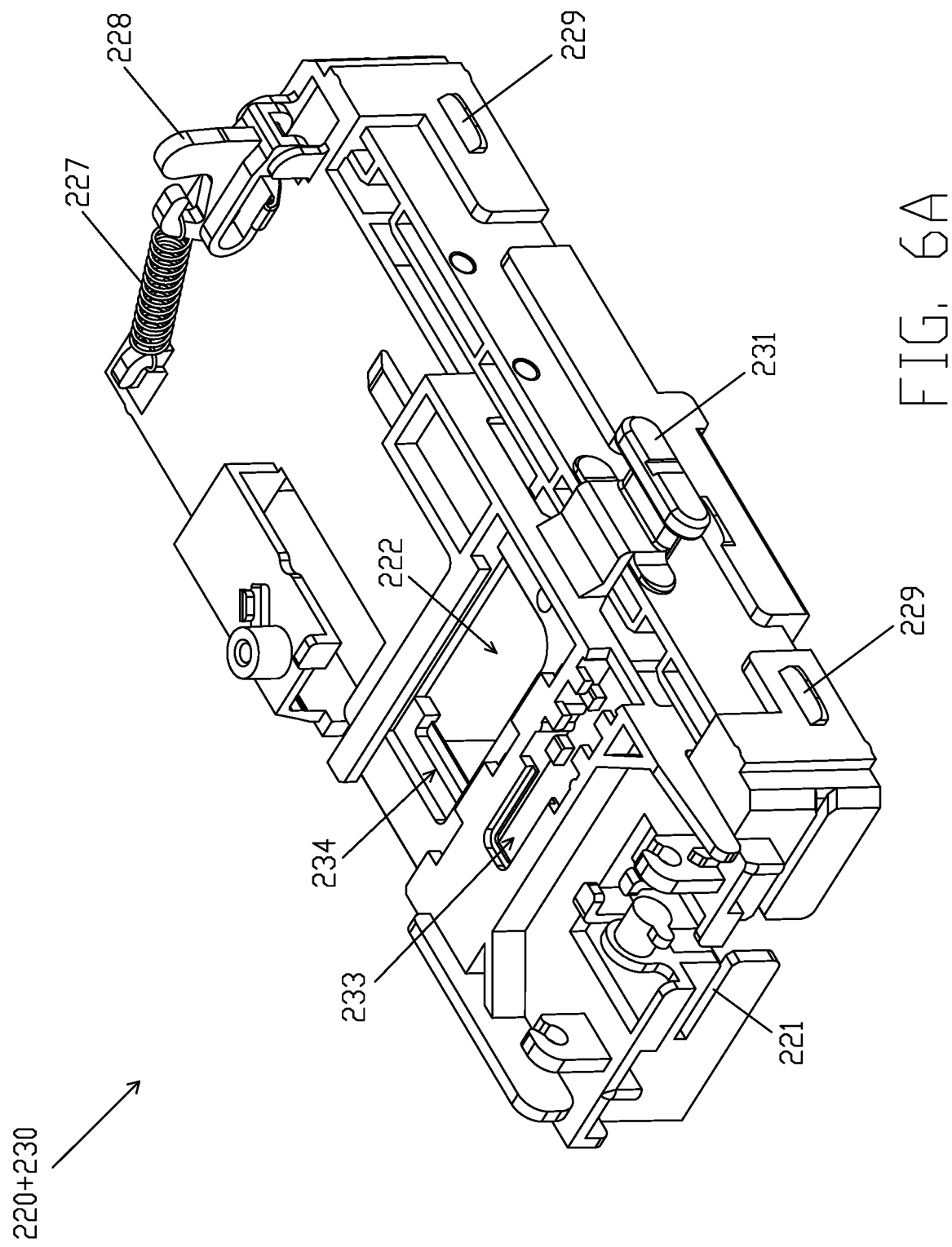

FIG. 6A illustrates a perspective view of main bracket 220 and test strip bracket 230 when test strip bracket 230 is in main bracket 220, according to some embodiments of the present disclosure. In conjunction with FIGS. 3A and 3B, handle 231 is operatively configured to maintain test strip bracket 230 in a first state with respect to main bracket 220 to align main detecting opening 222 of main bracket 220 with second detecting opening 234 of test strip adaptor 230.

Figure 6B:
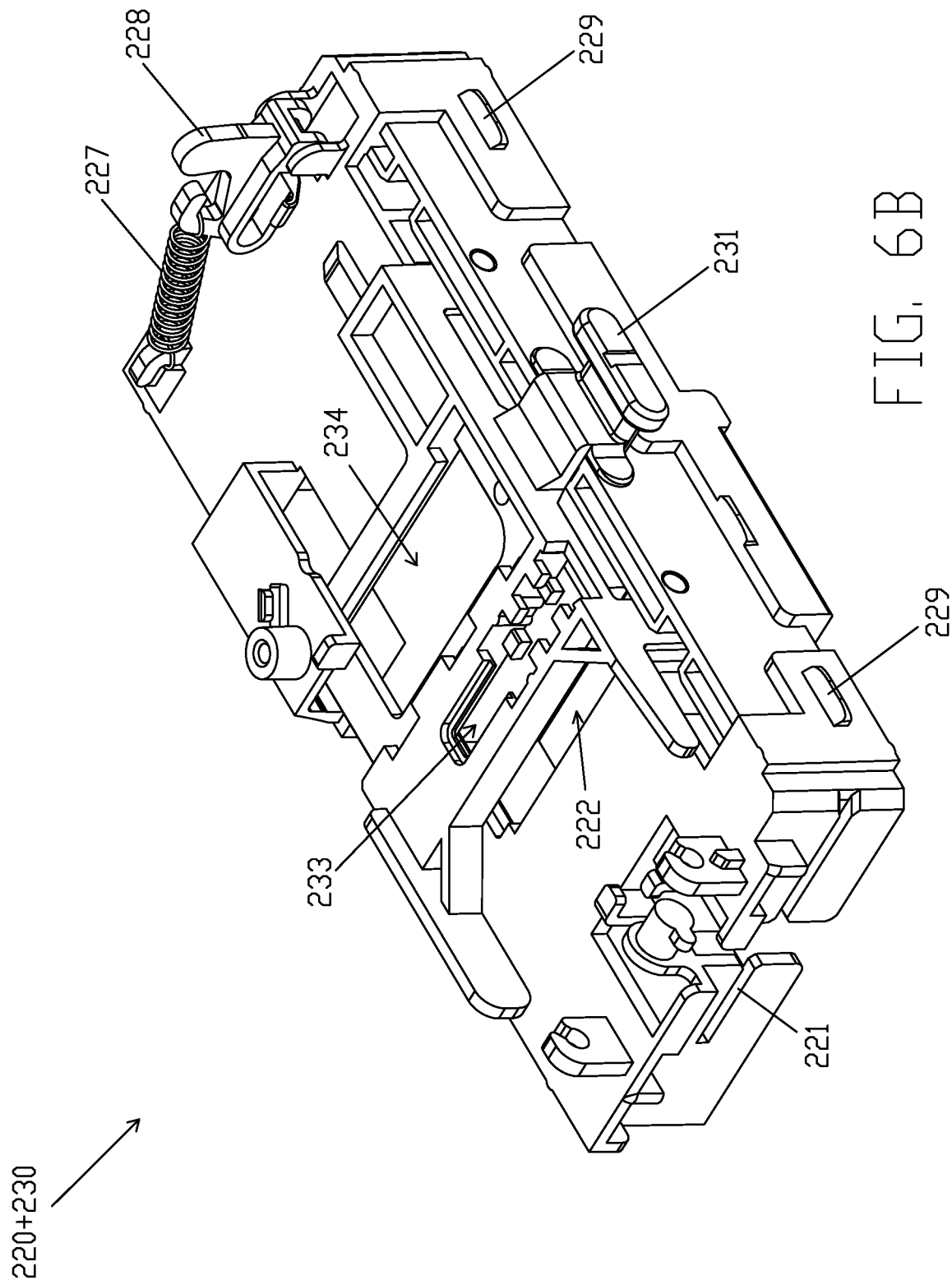

FIG. 6B illustrates another perspective view of main bracket 220 and test strip bracket 230 when test strip bracket 230 is in main bracket 220, according to some embodiments of the present disclosure. In conjunction with FIGS. 3A and 3B, handle 231 is operatively configured to maintain test strip bracket 230 in a second state with respect to main bracket 220 to align main detecting opening 222 of main bracket 220 with first detecting opening 233 of test strip adaptor 230.

FIG. 6C illustrates yet another perspective view of main bracket 220 and test strip bracket 230 when test strip bracket 230 is in main bracket 220, according to some embodiments of the present disclosure. In conjunction of FIGS. 3A and 3B, test strip bracket 230 is maintained in a third state with respect to main bracket 220 so that main bracket 220 is neither aligned with first detecting opening 233 nor with second detecting opening 234. In some embodiments, in the third state, main detecting opening 222 is at least partially unobstructed from second door 226.

Figure 7A:
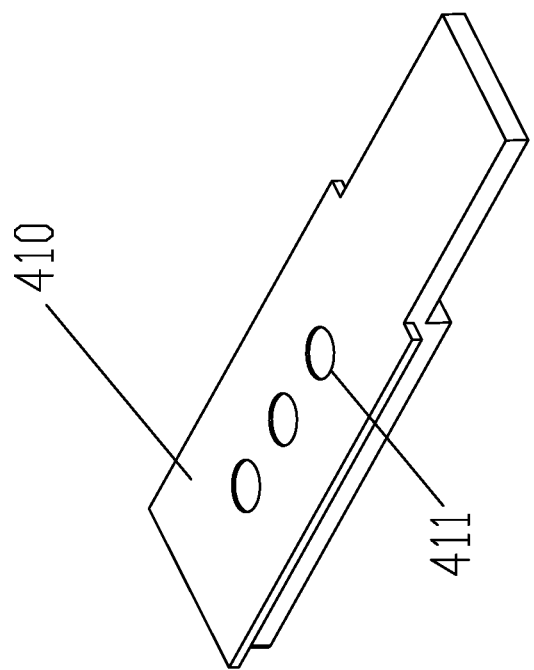
FIGS. 7A, 7B, 7C and 7D illustrate different type of test strips, according to some embodiments of the present disclosure.
Figure 7A:
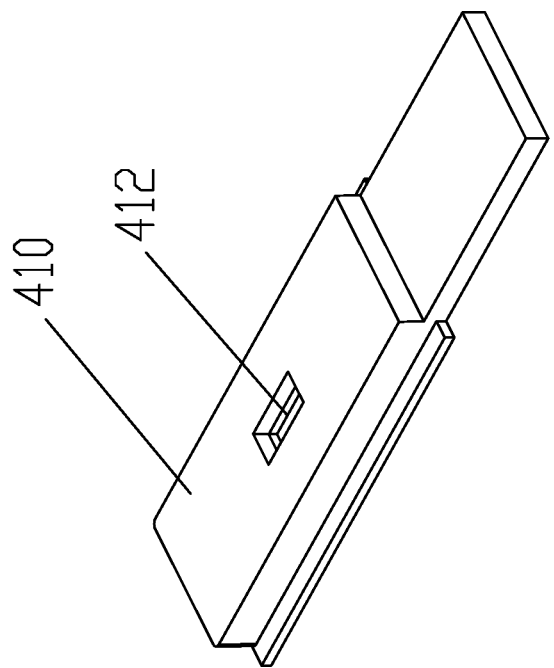
Figure 7B:
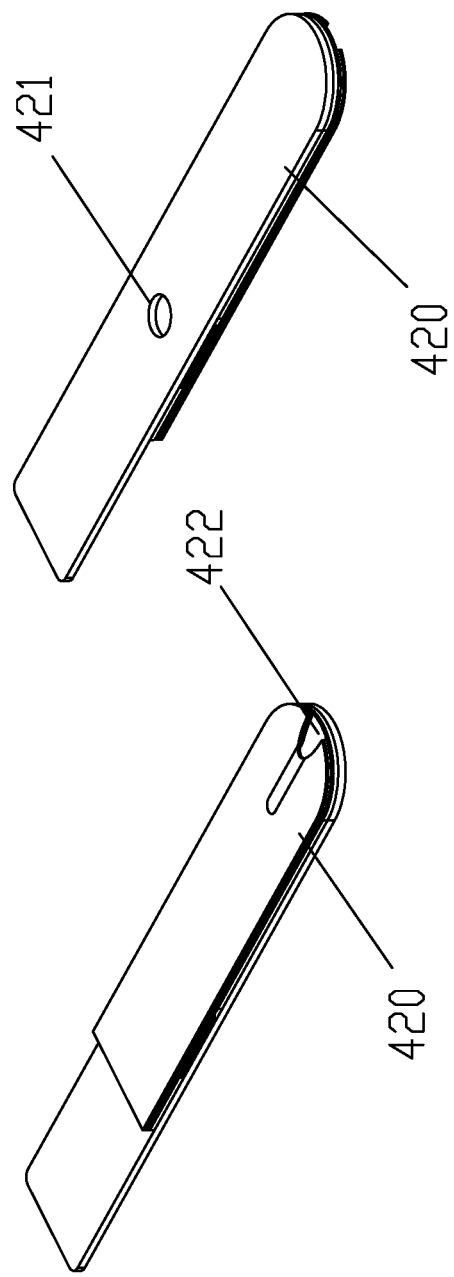
Figure 7C:
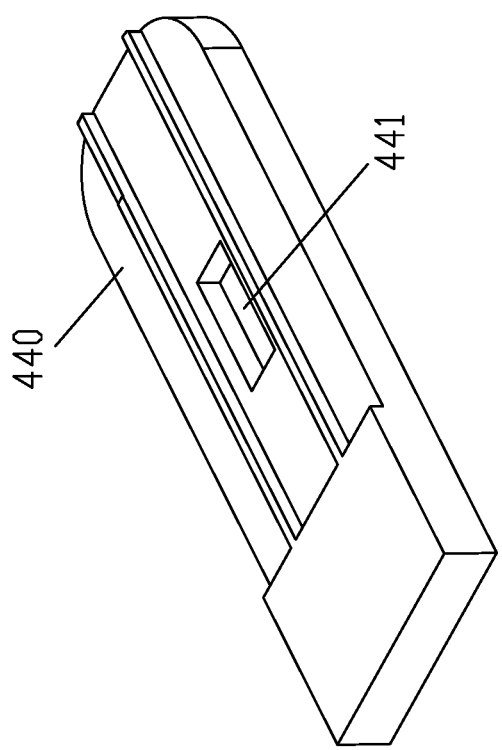
Figure 7C:
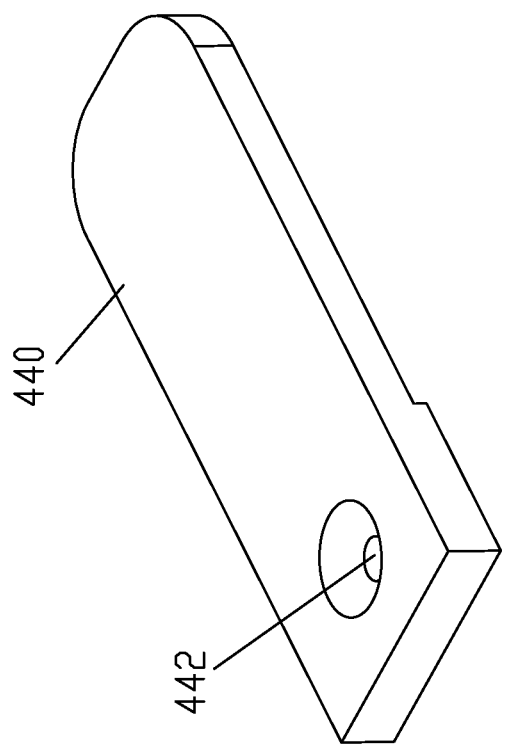

FIGS. 7A, 7B, 7C and 7D illustrate different type of test strips according to some embodiments of the present disclosure. FIG. 7A illustrates two perspective views of middle sized test strip 410. Middle sized test strip 410 may include multiple reaction areas 411 and sample collector 412. FIG. 7B illustrates two perspective views of small sized test strip 420. Small sized test strip 420 may include a reaction area 421 and a sample collector 422. FIG. 7C illustrates two perspective views of large sized test strip 440. Large sized test strip 440 may include reaction area 441 and sample collector 442. In some embodiments, a sample may be disposed in sample collectors 412, 422 and 442.

Figure 7D:
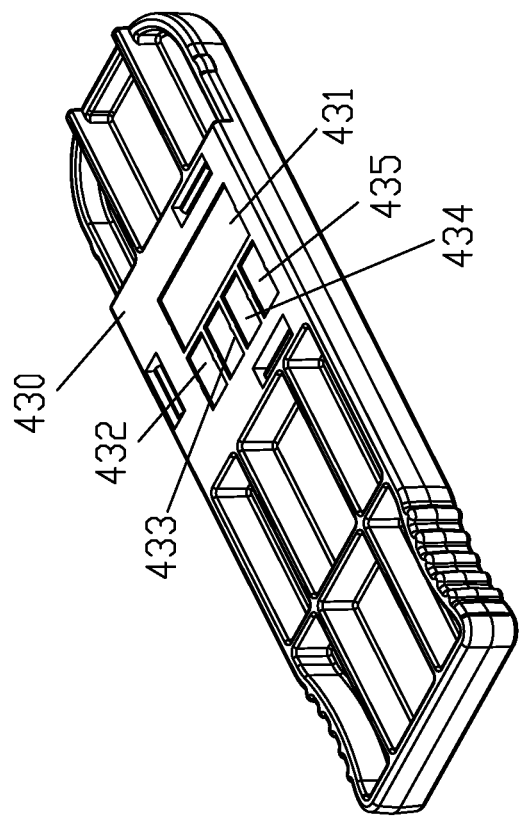
Figure 7D:
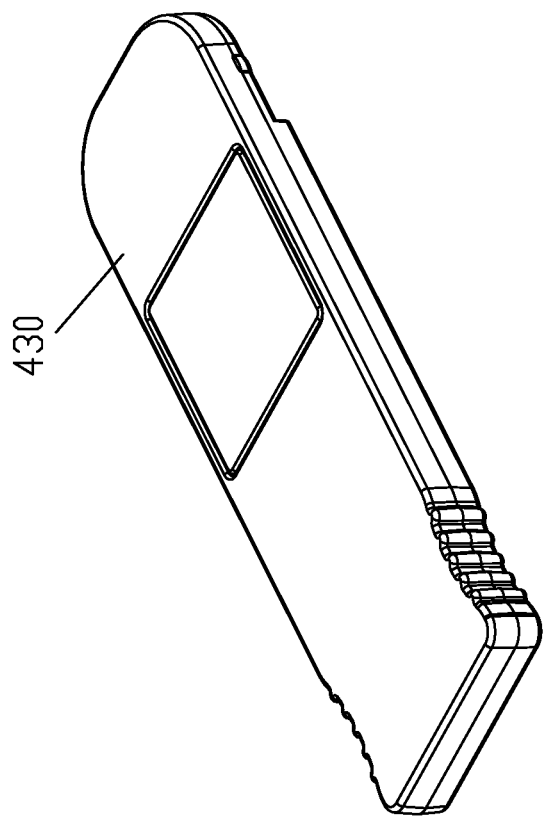

FIG. 7D illustrates two perspective views of calibration test strip 430. In some embodiments, calibration test strip 430 includes white calibration block 431, red color similar calibration blocks 432 and 433 (e.g., maroon calibration block and red calibration block) and green/blue color similar calibration blocks 434 and 435 (e.g., green calibration block and blue calibration block). A light to be used in illuminating the sample may be calibrated with calibration blocks 431, 432, 433, 434 and 435. In some embodiments, the red component included in the light may be calibrated by comparing one or more reflectance associated with red color similar calibration blocks 432 and 433 against one or more reflectance associated with white calibration block 431. In response to the comparison exceeding a predetermined range, the light (e.g., light from screen 320 of mobile device 300) is determined to be not suitable for illuminating the sample as the calibration result. Similarly, the green/blue components included in the light may be calibrated by comparing one or more reflectance associated with green/blue color similar calibration blocks 434 and 435 against one or more reflectance associated with white calibration block 431. In response to the comparison exceeding a predetermined range, the light is determined to be not suitable for illuminating the sample as the calibration result and another mobile device may be used to provide the light source instead of mobile device 300.

Figure 8A:
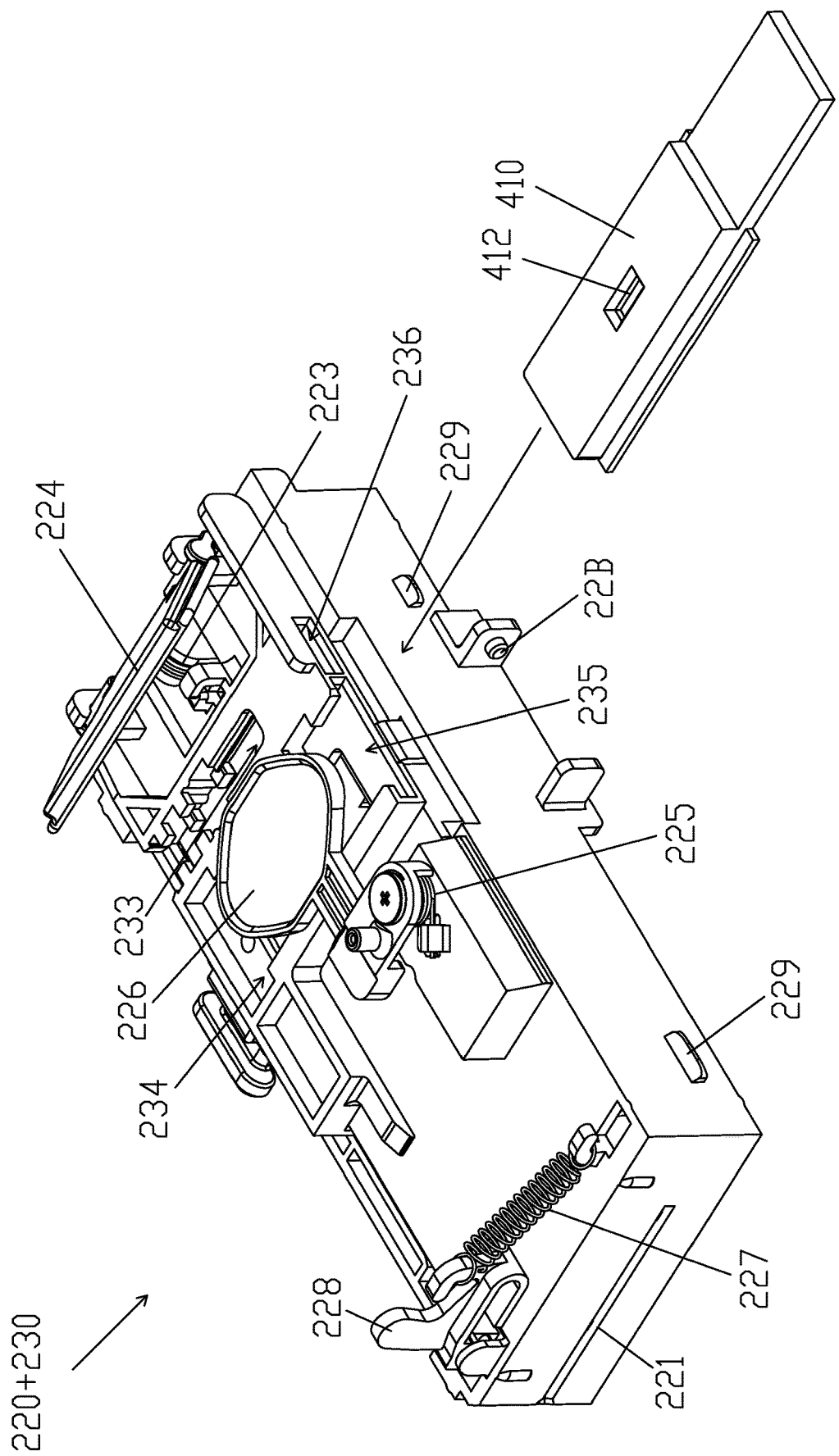
FIG. 8A illustrates a front perspective view of main bracket 220 and test strip bracket 230 prior to middle sized test strip 410 being inserted into second detecting opening 234 and second inserting entry 215, according to some embodiments of the present disclosure.
Figure 8B:
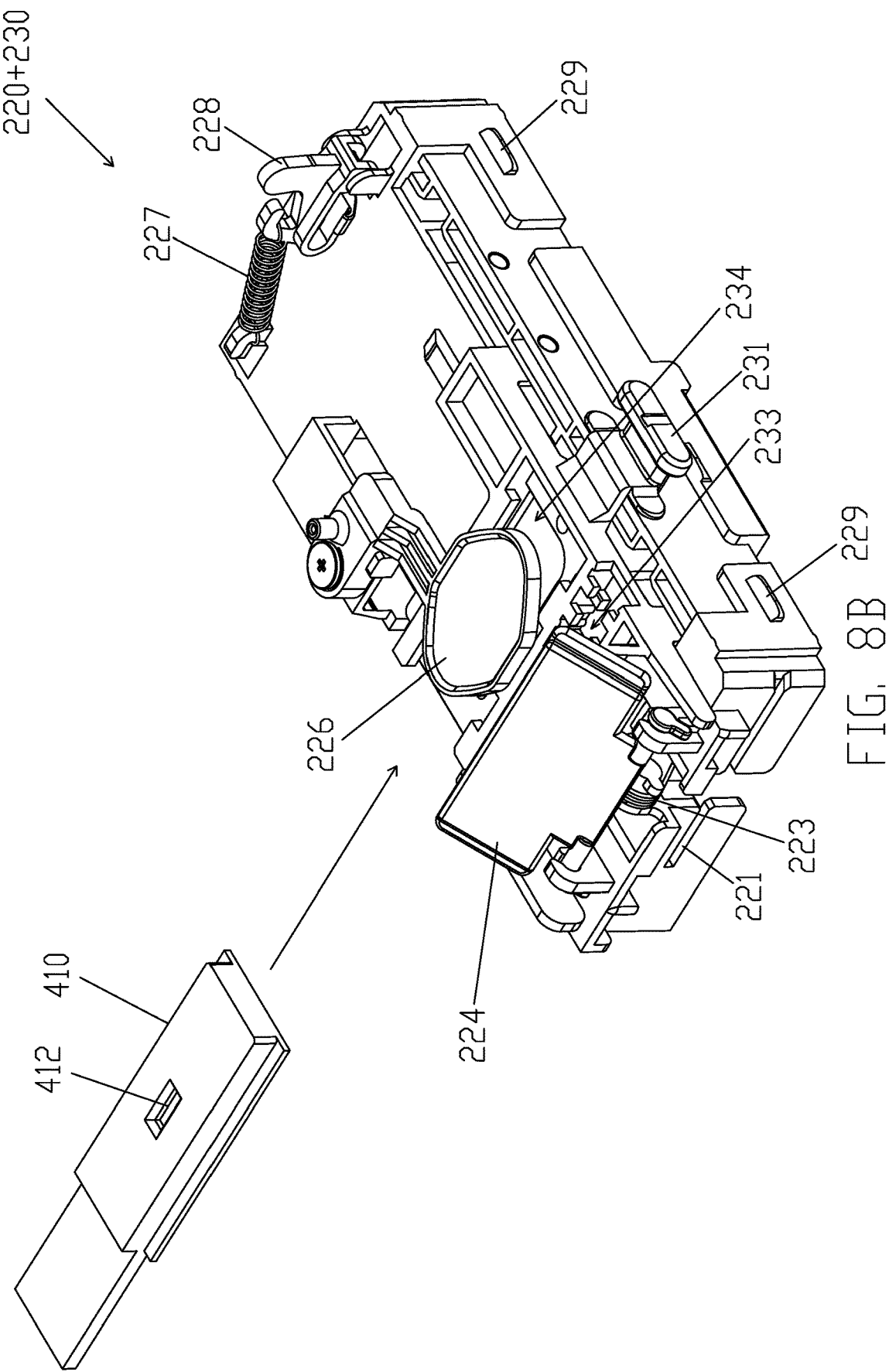
FIG. 8B illustrates back perspective view of main bracket 220 and test strip bracket 230 prior to middle sized test strip 410 being inserted into second detecting opening 234 and second inserting entry 215, according to some embodiments of the present disclosure.
Figure 8C:
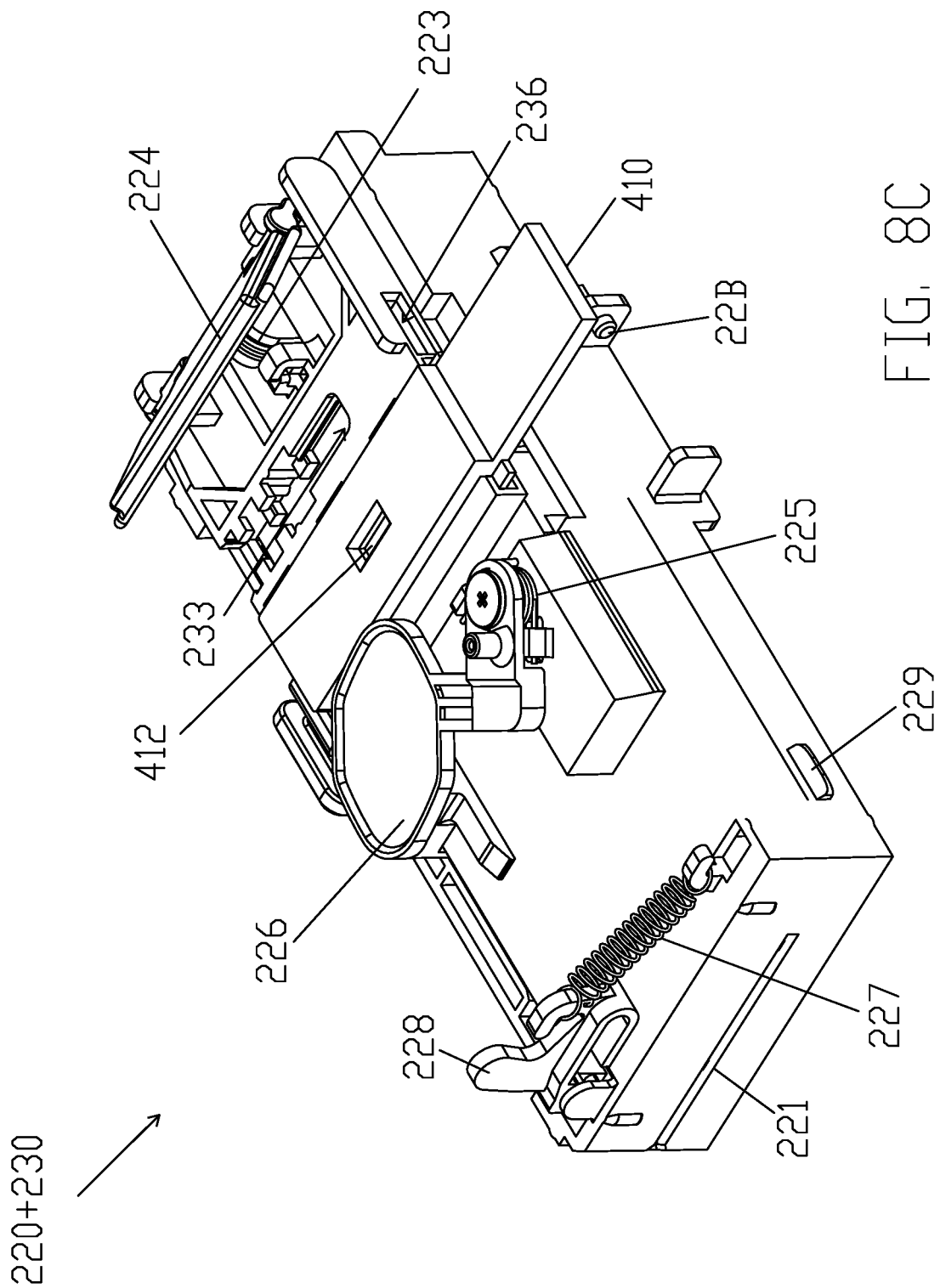
FIG. 8C illustrates front perspective view of main bracket 220 and test strip bracket 230 after middle sized test strip 410 being inserted into second detecting opening 234 and second inserting entry 215, according to some embodiments of the present disclosure.
Figure 8D:
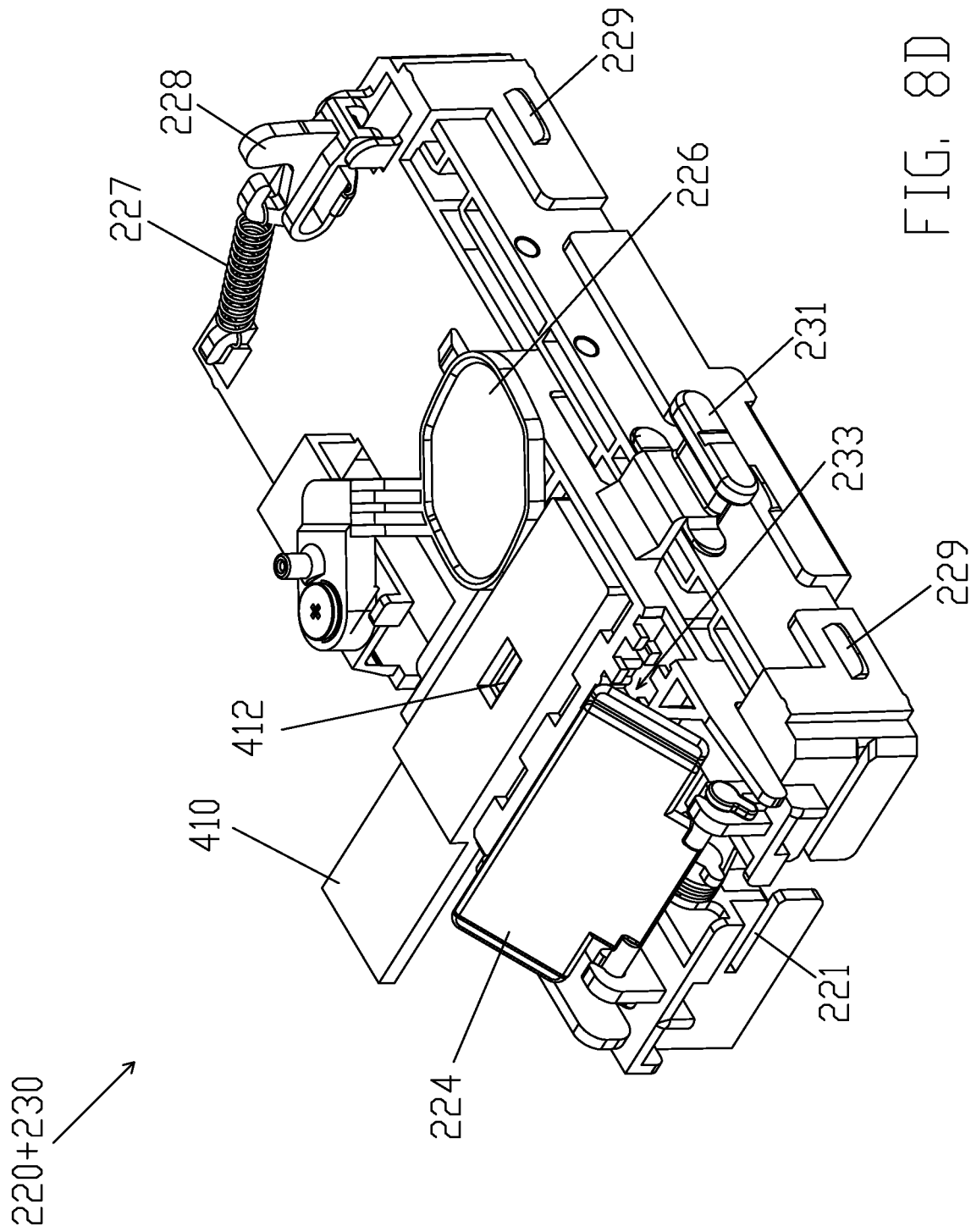
FIG. 8D illustrates back perspective view of main bracket 220 and test strip bracket 230 after middle sized test strip 410 being inserted into second detecting opening 234 and second inserting entry 215, according to some embodiments of the present disclosure.

FIG. 8A illustrates front perspective view of main bracket 220 and test strip bracket 230 prior to middle sized test strip 410 being inserted into second detecting opening 234 and second inserting entry 215, according to some embodiments of the present disclosure. FIG. 8B illustrates back perspective view of main bracket 220 and test strip bracket 230 prior to middle sized test strip 410 being inserted into second detecting opening 234 and second inserting entry 215, according to some embodiments of the present disclosure. FIG. 8C illustrates front perspective view of main bracket 220 and test strip bracket 230 after middle sized test strip 410 being inserted into second detecting opening 234 and second inserting entry 215, according to some embodiments of the present disclosure. FIG. 8D illustrates back perspective view of main bracket 220 and test strip bracket 230 after middle sized test strip 410 being inserted into second detecting opening 234 and second inserting entry 215, according to some embodiments of the present disclosure.

In some embodiments, in conjunction with FIG. 3B, in response to middle sized test strip 410 being inserted into second inserting entry 215 (illustrated in FIG. 3B) and second detecting opening 234, middle sized test strip 410 may push second door 226 from the first position of second door 226 to the second position of second door 226 to reveal main detecting opening 222. Therefore, in conjunction with FIG. 6A, main detecting opening 222 is aligned with second detecting opening 234. In addition, entry 235 of second detecting opening 234 includes a first shape corresponding to second inserting entry 215 to receive middle sized test strip 410 and not test strips having different sizes from middle sized test strip 410.

In some embodiments, in response to middle sized test strip 410 being inserted into second inserting entry 215 and second detecting opening 234, reaction area 411 of middle sized test strip 410 is aligned with second detecting opening 234 and main detecting opening 222. In some embodiments, in conjunction with FIGS. 1, 2A, 3B and 3C, light from screen 320 is configured to pass through illuminating screen opening 112, light guide illuminating opening 242, main detecting opening 222 and second detecting opening 234 in sequence, and eventually illuminate reaction area 411. Camera 310 is also configured to capture images of reaction area 411 through second detecting opening 234, main detecting opening 222, light guide opening 241 and camera hole 111 in sequence. The capture images are then analyzed to obtain the concentration of an analyte (e.g., blood glucose) in the sample.

Figure 9B:
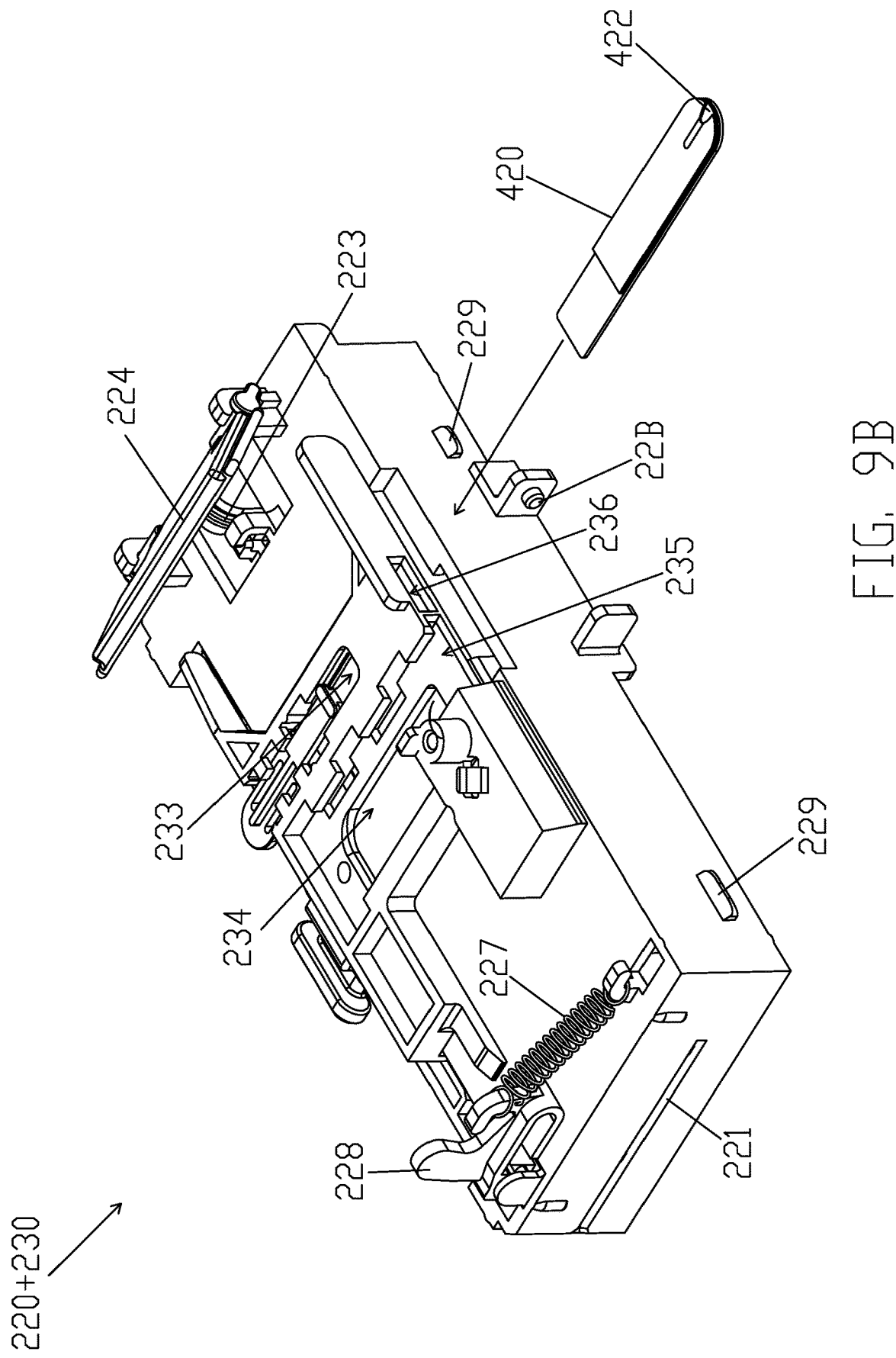
FIG. 9B illustrates back perspective view of main bracket 220 and test strip bracket 230 prior to small sized test strip 420 being inserted into first detecting opening 233 and second inserting entry 215, according to some embodiments of the present disclosure.

FIG. 9A illustrates front perspective view of main bracket 220 and test strip bracket 230 prior to small sized test strip 420 being inserted into first detecting opening 233 and second inserting entry 215, according to some embodiments of the present disclosure. FIG. 9B illustrates back perspective view of main bracket 220 and test strip bracket 230 prior to small sized test strip 420 being inserted into first detecting opening 233 and second inserting entry 215, according to some embodiments of the present disclosure. FIG. 9C illustrates front perspective view of main bracket 220 and test strip bracket 230 after small sized test strip 420 being inserted into first detecting opening 233 and second inserting entry 215, according to some embodiments of the present disclosure. FIG. 9D illustrates back perspective view of main bracket 220 and test strip bracket 230 after small sized test strip 420 being inserted into first detecting opening 233 and second inserting entry 215, according to some embodiments of the present disclosure.

In some embodiments, in conjunction with FIG. 3A, in response to small sized test strip 420 being inserted into second inserting entry 215 (illustrated in FIG. 3B) and first detecting opening 233, small sized test strip 420 may be placed underneath second door 226 and second door 226 is maintained at the first position of second door 226. Therefore, in conjunction with FIG. 6B, main detecting opening 222 is aligned with first detecting opening 233 free from the block of second door 226. In addition, entry 236 of third detecting opening 233 includes a second shape corresponding to second inserting entry 215 to receive small sized test strip 420 and not test strips having different sizes from small sized test strip 420

In some embodiments, in response to small sized test strip 420 being inserted into second inserting entry 215 and first detecting opening 233, reaction area 421 of small sized test strip 420 is aligned with first detecting opening 233 and main detecting opening 222. In some embodiments, in conjunction with FIGS. 1, 2A, 3A and 3C, light from screen 320 is configured to pass through illuminating screen opening 112, light guide illuminating opening 242, main detecting opening 222 and first detecting opening 233 in sequence, and eventually illuminate reaction area 421. Camera 310 is also configured to capture images of reaction area 421 through first detecting opening 233, main detecting opening 222, light guide opening 241 and camera hole 111 in sequence. The capture images are then analyzed to obtain the concentration of an analyte (e.g., blood glucose) in the sample.

Figure 10A:
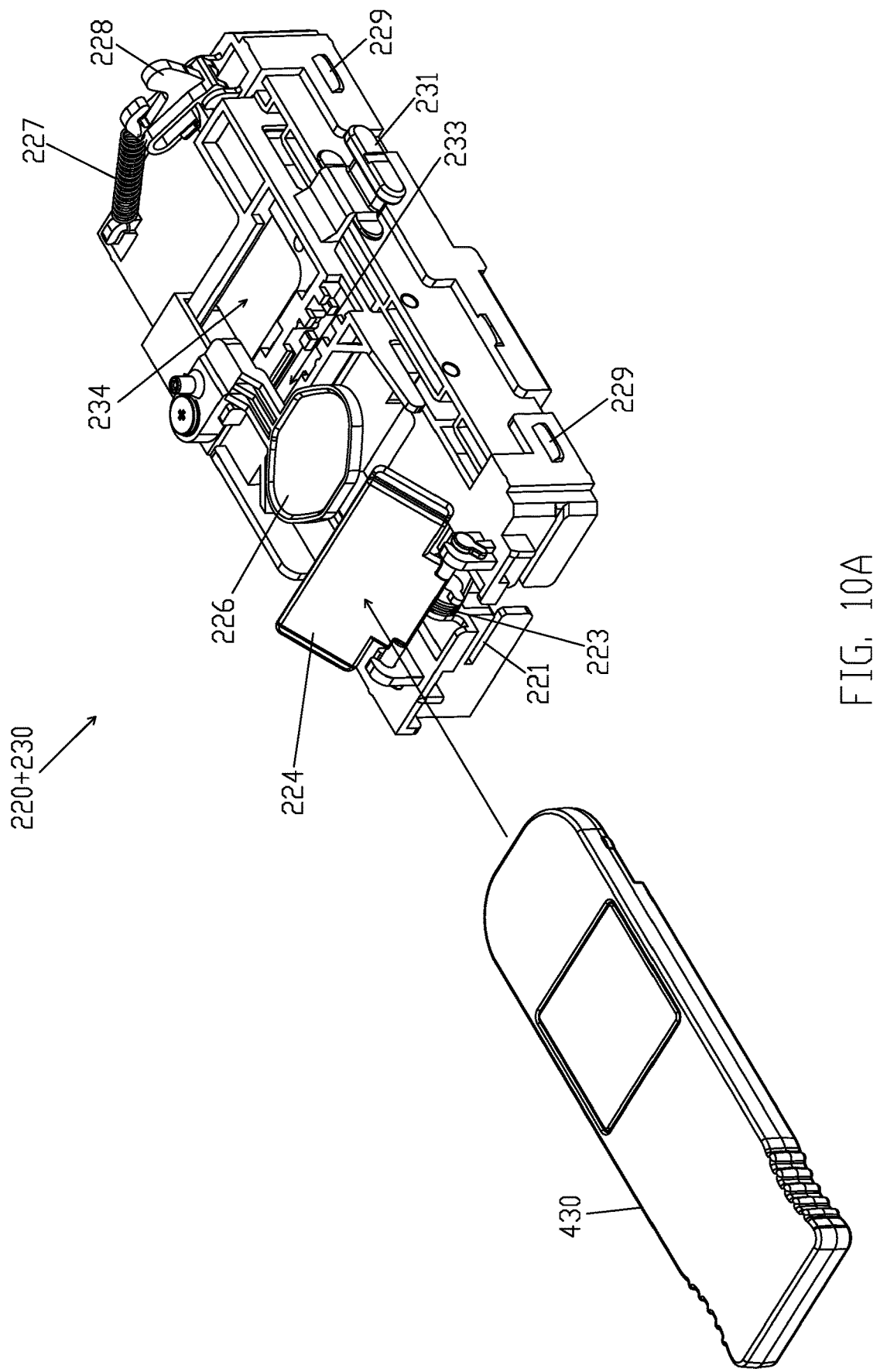
FIG. 10A illustrates front perspective view of main bracket 220 and test strip bracket 230 prior to calibration test strip 430 being inserted into first inserting entry 214, according to some embodiments of the present disclosure.
Figure 10B:
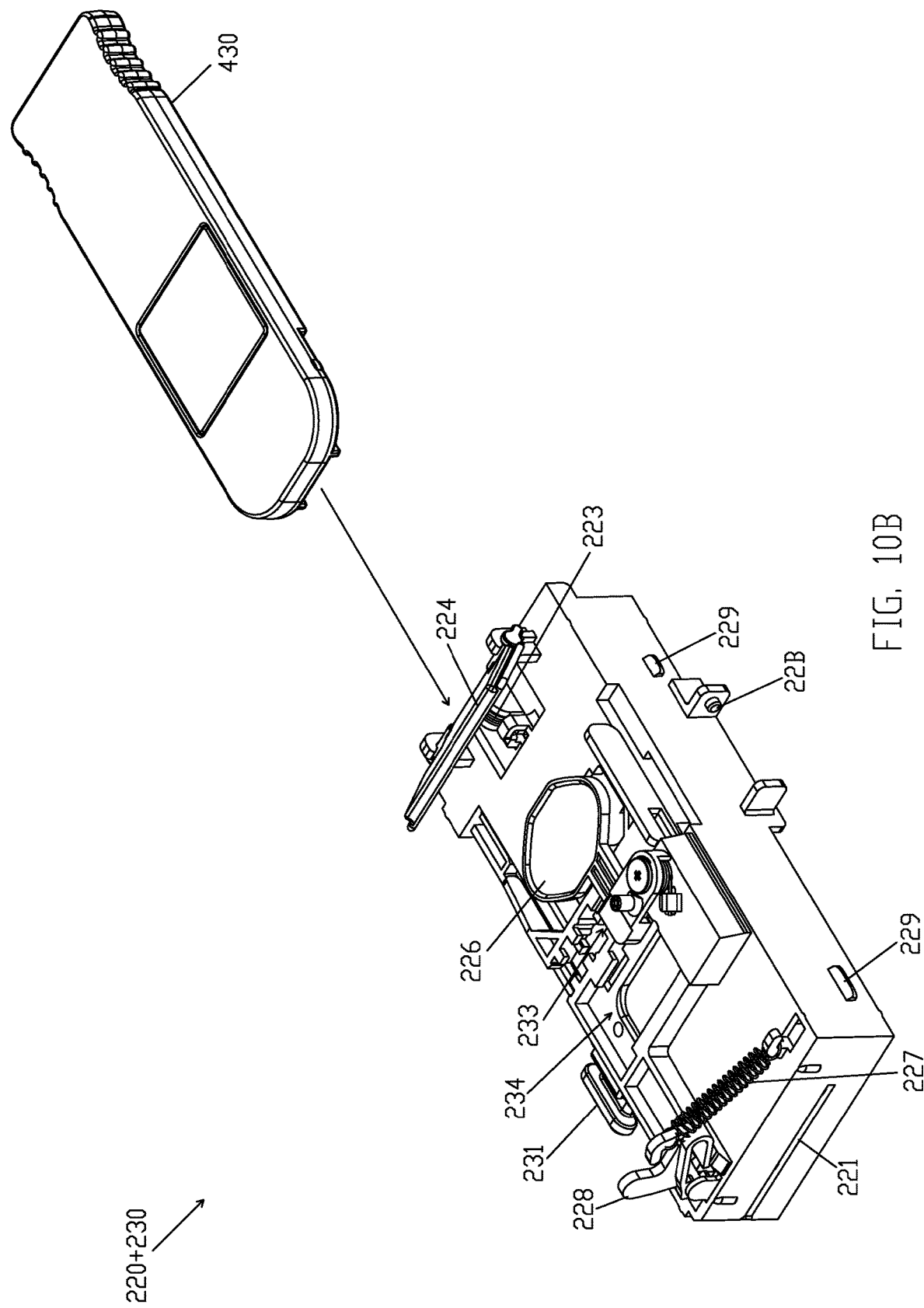
FIG. 10B illustrates back perspective view of main bracket 220 and test strip bracket 230 prior to calibration test strip 430 being inserted into first inserting entry 214, according to some embodiments of the present disclosure.
Figure 10D:
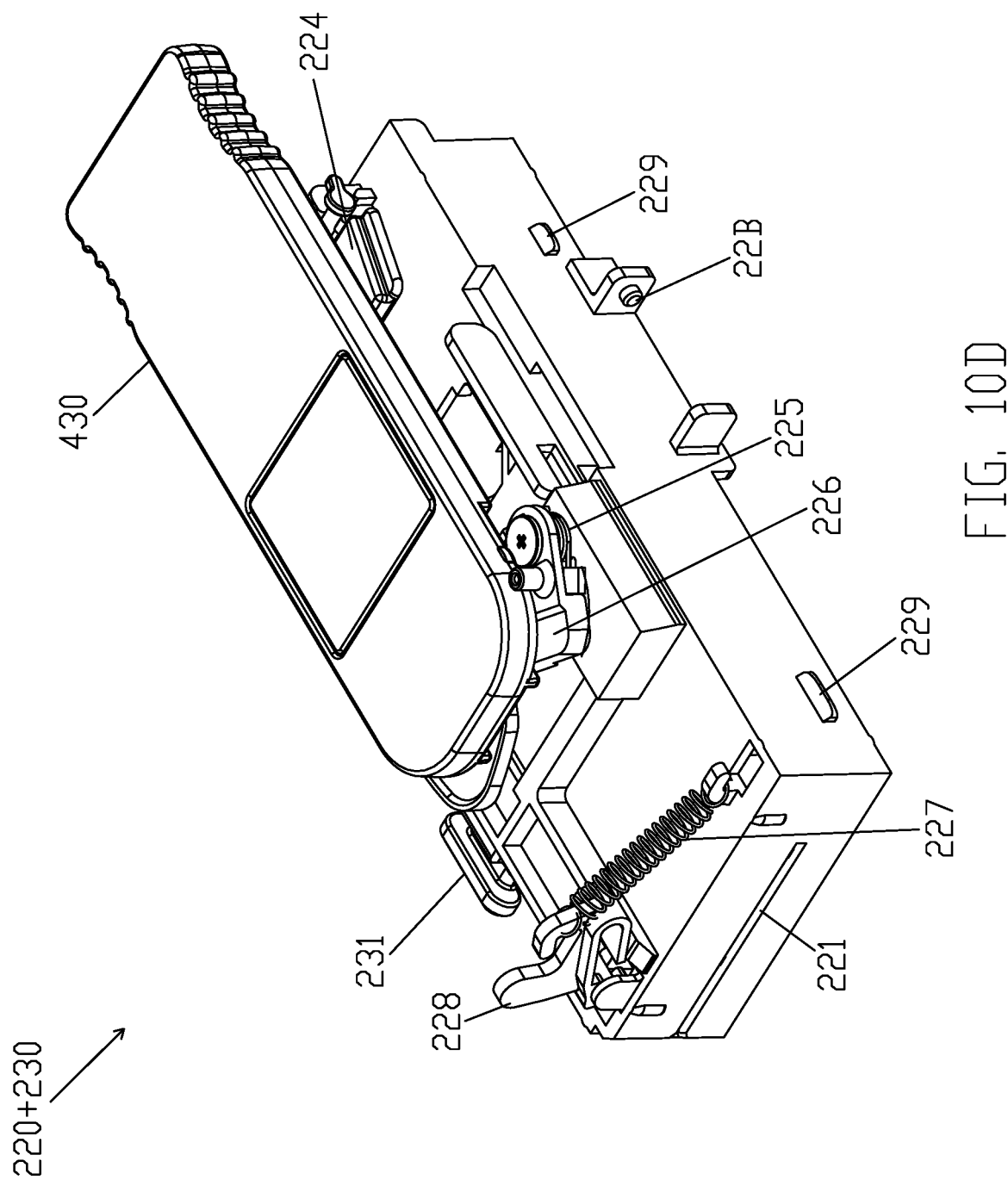
FIG. 10D illustrates back perspective view of main bracket 220 and test strip bracket 230 after calibration test strip 430 being inserted into first inserting entry 214, according to some embodiments of the present disclosure.

FIG. 10A illustrates front perspective view of main bracket 220 and test strip bracket 230 prior to calibration test strip 430 being inserted into first inserting entry 214, according to some embodiments of the present disclosure. FIG. 10B illustrates back perspective view of main bracket 220 and test strip bracket 230 prior to calibration test strip 430 being inserted into first inserting entry 214, according to some embodiments of the present disclosure. FIG. 10C illustrates front perspective view of main bracket 220 and test strip bracket 230 after calibration test strip 430 being inserted into first inserting entry 214, according to some embodiments of the present disclosure. FIG. 10D illustrates back perspective view of main bracket 220 and test strip bracket 230 after calibration test strip 430 being inserted into first inserting entry 214, according to some embodiments of the present disclosure.

In some embodiments, in conjunction with FIG. 3A, in response to calibration test strip 430 being inserted into first inserting entry 214, calibration test strip 430 may push first door 224 and second door 226. By pushing second door 226 from the first position of second door 226 to the second position of second door 226, main detecting opening 222 is at least partially unobstructed from second door 226. In conjunction with FIG. 6C, a part of calibration test strip 430 (e.g., calibration blocks 431, 432, 433, 434 and 435) may be disposed above and aligned with main detecting opening 222.

In some embodiments, in conjunction with FIGS. 1, 2A, 3A and 3C, light from screen 320 is configured to pass through illuminating screen opening 112, light guide illuminating opening 242 and main detecting opening 222 in sequence, and eventually illuminate calibration blocks 431, 432, 433, 434 and 435 of calibration test strip 430. Camera 310 is also configured to capture images of calibration blocks 431, 432, 433, 434 and 435 through main detecting opening 222, light guide camera opening 241 and camera hole 111 in sequence. As set forth above, the capture images are then analyzed to determine whether light from screen 320 is a suitable light source for physiological measurement. In some embodiments, some example physiological measurements are illustrated in FIGS. 8A, 8B, 9A, 9B, 11A and 11B.

Figure 11A:
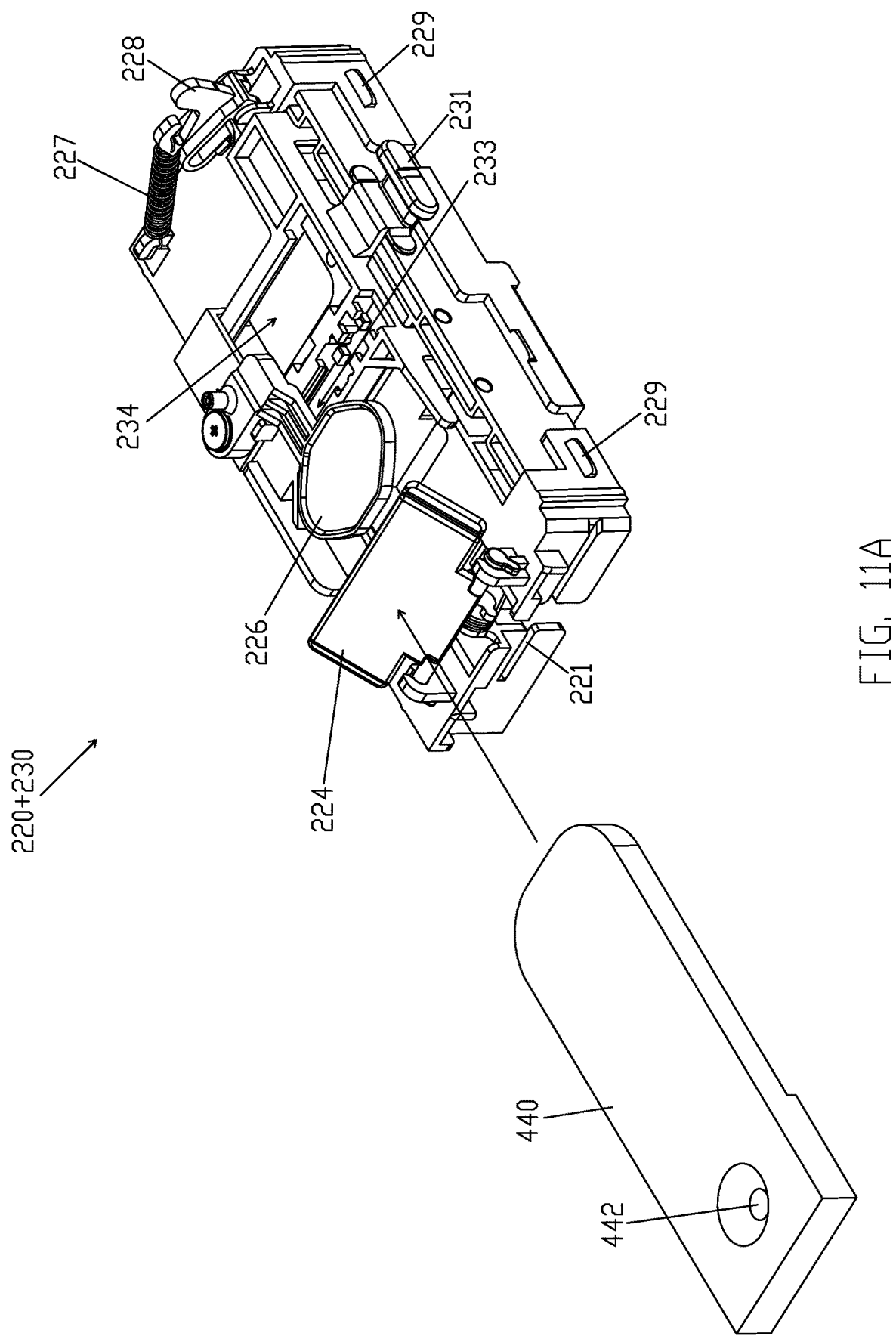
FIG. 11A illustrates front perspective view of main bracket 220 and test strip bracket 230 prior to large sized test strip 440 being inserted into first inserting entry 214, according to some embodiments of the present disclosure.
Figure 11B:
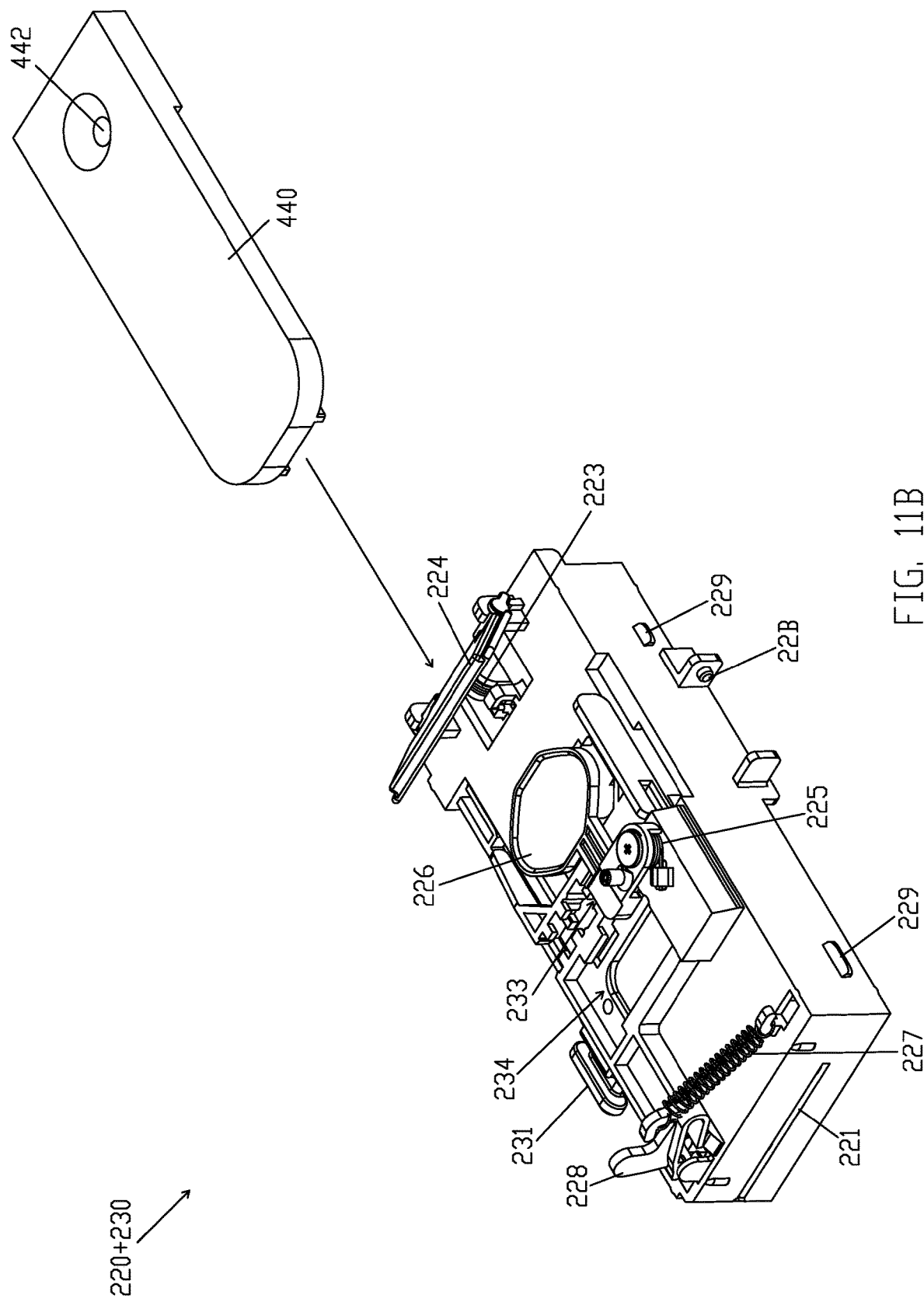
FIG. 11B illustrates back perspective views of main bracket 220 and test strip bracket 230 prior to large sized test strip 440 being inserted into first inserting entry 214, according to some embodiments of the present disclosure.
Figure 11C:
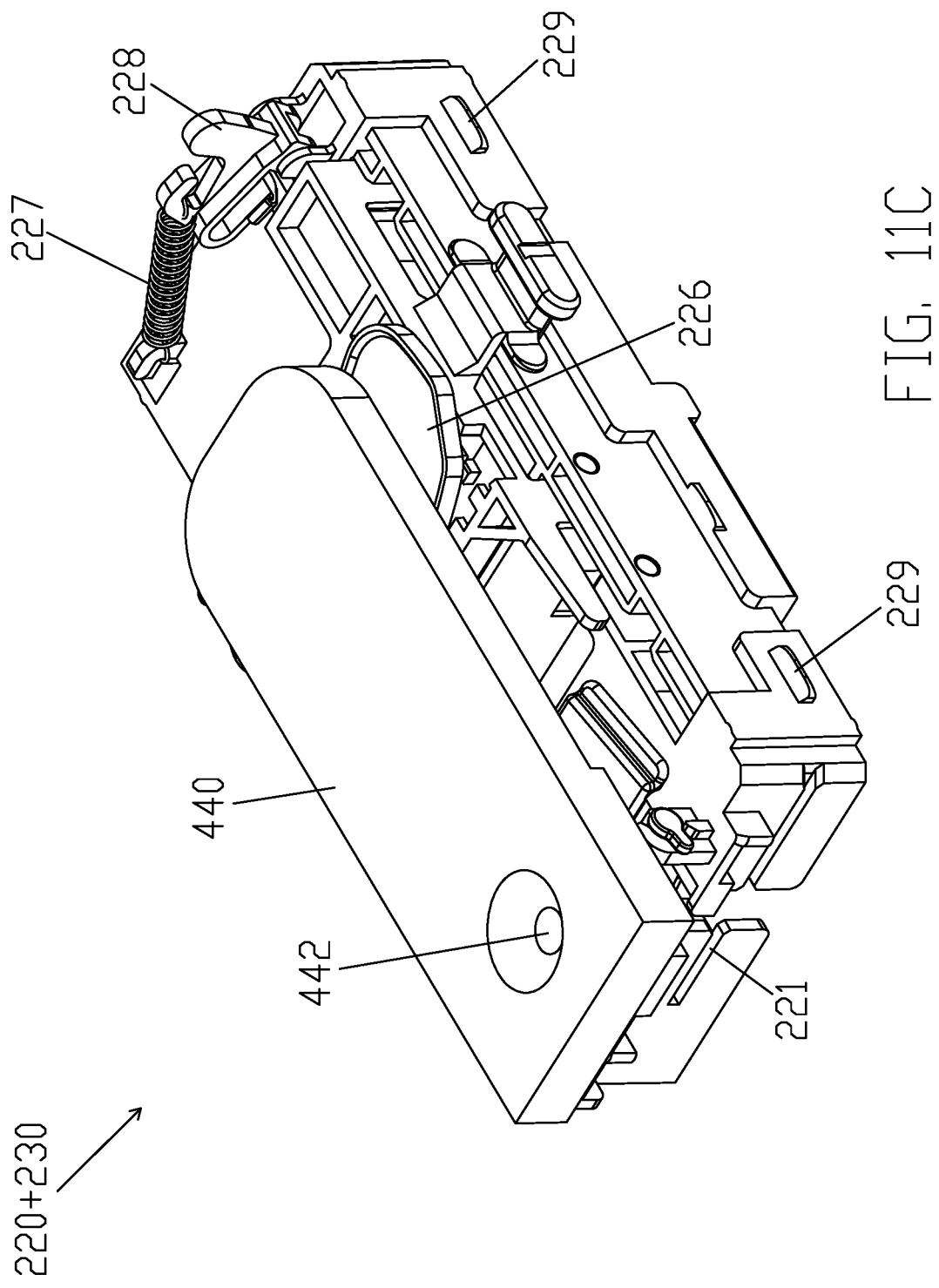
FIG. 11C illustrates front perspective view of main bracket 220 and test strip bracket 230 after large sized test strip 440 being inserted into first inserting entry 214, according to some embodiments of the present disclosure.
Figure 11D:
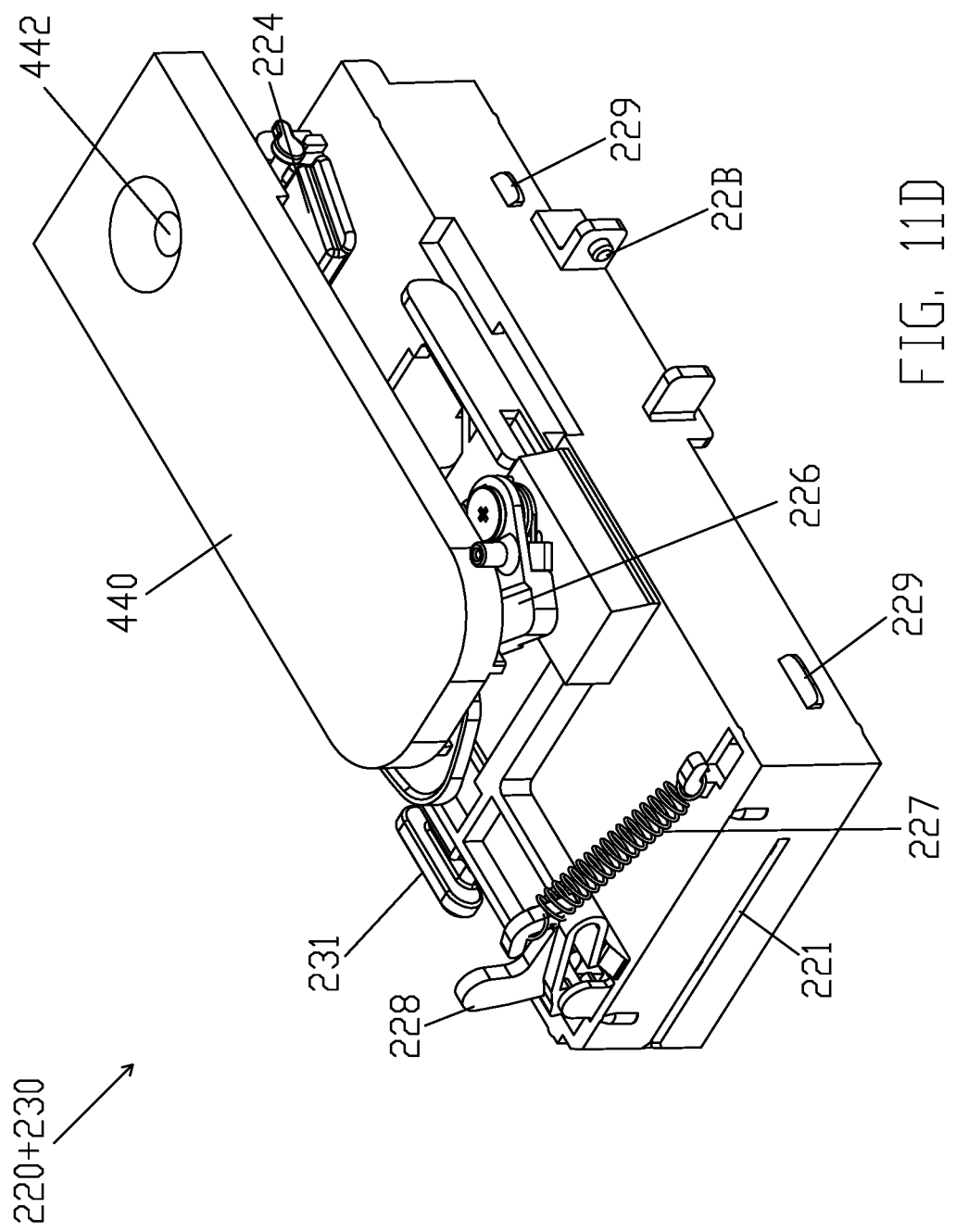
FIG. 11D illustrates back perspective view of main bracket 220 and test strip bracket 230 after large sized test strip 440 being inserted into first inserting entry 214, according to some embodiments of the present disclosure.

FIG. 11A illustrates front perspective view of main bracket 220 and test strip bracket 230 prior to large sized test strip 440 being inserted into first inserting entry 214, according to some embodiments of the present disclosure. FIG. 11B illustrates back perspective views of main bracket 220 and test strip bracket 230 prior to large sized test strip 440 being inserted into first inserting entry 214, according to some embodiments of the present disclosure. FIG. 11C illustrates front perspective view of main bracket 220 and test strip bracket 230 after large sized test strip 440 being inserted into first inserting entry 214, according to some embodiments of the present disclosure. FIG. 11D illustrates back perspective view of main bracket 220 and test strip bracket 230 after large sized test strip 440 being inserted into first inserting entry 214, according to some embodiments of the present disclosure.

In some embodiments, in conjunction with FIG. 3A, in response to large sized test strip 440 being inserted into first inserting entry 214, large sized test strip 440 may push first door 224 and second door 226. By pushing second door 226 from the first position of second door 226 to the second position of second door 226, main detecting opening 222 is at least partially unobstructed from second door 226. In conjunction with FIG. 6C, reaction area 442 of large sized test strip 440 may be disposed above and aligned with main detecting opening 222.

In some embodiments, in conjunction with FIGS. 1, 2A, 3A and 3C, light from screen 320 is configured to pass through illuminating screen opening 112, light guide illuminating opening 242 and main detecting opening 222 in sequence, and eventually illuminate reaction area 442 of large sized test strip 440. Camera 310 is also configured to capture images of reaction area 442 through main detecting opening 222, light guide camera opening 241 and camera hole 111 in sequence. The capture images are then analyzed to obtain the concentration of an analyte (e.g., blood glucose) in the sample.

As set forth above, in some embodiments, test strip adaptor 200 includes at least two inserting entries (e.g., first inserting entry 214 and second inserting entry 215) and at least three detecting opening (e.g., main detecting opening 222, first detecting opening 233, second detecting opening 234) to receive different types of test strips (e.g., test strips 410, 420, 430 and 440). There is no need for an user to change test strip adaptors to fit different types of test strips.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. An accessory for a mobile device to measure characteristics of a test strip, the accessory comprising:
   a mobile device adapter defining a camera hole and an illuminating screen opening; and
   a test strip adapter configured to lock to the mobile device adapter, the test strip adaptor comprising:
      a case defining a first inserting entry and a second inserting entry to receive a test strip;
      a main bracket configured to engage with the case and defining a main detecting opening that corresponds to the camera hole and the illuminating screen opening; and
      a test strip bracket disposed in the main bracket and configured to receive the test strip inserted via the first inserting entry or the second inserting entry.

2. The accessory of claim 1, wherein the main bracket further comprises:
   a first connecting element engaged with the case; and
   a second connecting element and a pivot.

3. The accessory of claim 2, wherein the case further defines a connecting opening to engage with the first connecting element.

4. An accessory for a mobile device to measure characteristics of a test strip, the accessory comprising:
   a mobile device adapter defining a camera hole and an illuminating screen opening; and a test strip adapter configured to couple to the mobile device adapter, the test strip adaptor comprising:

a case that defines a first inserting entry and a second inserting entry to receive a test strip;

a main bracket configured to engage with the case, wherein the main bracket defines a main detecting opening that corresponds to the camera hole and the illuminating screen opening; and a test strip bracket configured to receive the test strip inserted from either the first inserting entry or the second inserting entry, wherein the test strip bracket defines at least one detecting opening.

5. The accessory of claim 4, wherein the main bracket further comprises a first door engaged with a first torsion spring, and the first door is operatively configured to move in response to the test strip being inserted from the first inserting entry.

6. The accessory of claim 5, wherein the main bracket further comprises a second door, which when the second door is in a first position on the main bracket, the second door covers the main detecting opening, and in response to the test strip being inserted from the second inserting entry, the second door is operatively configured to mow to a second position on the main bracket to leave the main detecting opening at least partially unobstructed.

7. The accessory of claim 6, wherein the test strip bracket further comprises a handle operatively configured to maintain the test strip bracket in a first state or a second state with respect to the main bracket, wherein:

in the first state, the at least one detecting opening is configured to align with the main detecting opening; and in the second state, the main detecting opening is revealed from the second door of the main bracket.

8. The accessory of claim 4, wherein the case further comprises a sliding module configured to slide from one side of the case to another side of the case to cover or reveal the second inserting entry.

9. The accessory of claim 8, wherein the main bracket further comprises a lock engaged with a tension spring on the main bracket to lock the sliding module.

* * * * *